United States Patent
Yun et al.

(10) Patent No.: US 9,594,036 B2
(45) Date of Patent: *Mar. 14, 2017

(54) X-RAY SURFACE ANALYSIS AND MEASUREMENT APPARATUS

(71) Applicant: Sigray, Inc., Concord, CA (US)

(72) Inventors: Wenbing Yun, Walnut Creek, CA (US); Sylvia Jia Yun Lewis, San Francisco, CA (US); Janos Kirz, Berkeley, CA (US)

(73) Assignee: Sigray, Inc., Concord, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/634,834

(22) Filed: Mar. 1, 2015

(65) Prior Publication Data
US 2015/0247811 A1    Sep. 3, 2015

Related U.S. Application Data

(60) Provisional application No. 61/946,475, filed on Feb. 28, 2014, provisional application No. 61/946,527, (Continued)

(51) Int. Cl.
*H01J 35/08*    (2006.01)
*G01N 23/223*    (2006.01)
(Continued)

(52) U.S. Cl.
CPC ........... *G01N 23/223* (2013.01); *G01B 15/02* (2013.01); *G01N 23/063* (2013.01);
(Continued)

(58) Field of Classification Search
CPC ............. H01J 2235/087; H01J 35/02; H01J 2235/081; H01J 2235/086; H01J 35/08;
(Continued)

(56) References Cited

U.S. PATENT DOCUMENTS 1,203,495 A    10/1916    Coolidge
1,211,092 A    1/1917    Coolidge
(Continued)

FOREIGN PATENT DOCUMENTS

EP    0432568 A2    6/1991
EP    0751533 A1    1/1997
(Continued)

OTHER PUBLICATIONS

Wobrauschek et al., Micro XRF of light elements using a polycapillary lens and an ultra-thin window Silicon Drift Detector inside a vacuum chamber, 2005, International Centre for Diffraction Data 2005, Advances in X-ray Analysis, vol. 48, pp. 229-235.*

(Continued)

*Primary Examiner* — David J Makiya
*Assistant Examiner* — John Corbett
(74) *Attorney, Agent, or Firm* — Franklin Schellenberg

(57) ABSTRACT

This disclosure presents systems for total reflection x-ray fluorescence measurements that have x-ray flux and x-ray flux density several orders of magnitude greater than existing x-ray technologies. These may therefore useful for applications such as trace element detection and/or for total-reflection fluorescence analysis. The higher brightness is achieved in part by using designs for x-ray targets that comprise a number of microstructures of one or more selected x-ray generating materials fabricated in close thermal contact with a substrate having high thermal conductivity. This allows for bombardment of the targets with higher electron density or higher energy electrons, which leads to greater x-ray brightness and therefore greater x-ray flux. The high brightness/high flux source may then be coupled to an x-ray reflecting optical system, which can focus the high flux x-rays to a spots that can be as small as one micron, leading to high flux density.

31 Claims, 16 Drawing Sheets

Related U.S. Application Data filed on Feb. 28, 2014, provisional application No. 62/008,856, filed on Jun. 6, 2014, provisional application No. 62/086,132, filed on Dec. 1, 2014, provisional application No. 62/117,062, filed on Feb. 17, 2015.

(51) Int. Cl.

| | | |
|---|---|---|
| *G01B 15/02* | (2006.01) | |
| *G01N 23/207* | (2006.01) | |
| *G21K 1/06* | (2006.01) | |
| *H01J 35/14* | (2006.01) | |
| *G01N 23/06* | (2006.01) | |

(52) U.S. Cl.
CPC .......... *G01N 23/2076* (2013.01); *G21K 1/06* (2013.01); *H01J 35/08* (2013.01); *H01J 35/14* (2013.01); *G21K 2201/061* (2013.01); *G21K 2201/064* (2013.01); *H01J 2235/081* (2013.01); *H01J 2235/086* (2013.01)

(58) Field of Classification Search
CPC ......... H01J 35/14; G21K 1/06; G01N 23/201; G01N 23/223; G01N 2223/6116; G01N 23/063; G01N 23/2076; G01B 15/02; C07H 13/06; C07H 13/12; C07H 15/10; C07H 5/06

See application file for complete search history.

(56) References Cited

U.S. PATENT DOCUMENTS

| | | | |
|---|---|---|---|
| 1,215,116 | A | 2/1917 | Coolidge |
| 1,328,495 | A | 1/1920 | Coolidge |
| 1,355,126 | A | 10/1920 | Coolidge |
| 1,790,073 | A | 1/1931 | Pohl |
| 1,917,099 | A | 7/1933 | Coolidge |
| 1,946,312 | A | 2/1934 | Coolidge |
| 2,926,270 | A | 2/1960 | Zunick |
| 3,795,832 | A | 3/1974 | Holland |
| 4,227,112 | A | 10/1980 | Waugh |
| 4,266,138 | A | 5/1981 | Nelson, Jr. |
| 4,523,327 | A | 6/1985 | Eversole |
| 4,573,186 | A | 2/1986 | Reinhold |
| 4,940,319 | A | 7/1990 | Ueda et al. |
| 4,951,304 | A | 8/1990 | Piestrup et al. |
| 4,972,449 | A | 11/1990 | Upadhya et al. |
| 5,001,737 | A | 3/1991 | Lewis |
| 5,008,918 | A | 4/1991 | Lee |
| 5,148,462 | A | 9/1992 | Spitsyn et al. |
| 5,249,216 | A | 9/1993 | Ohsugi |
| 5,276,724 | A | 1/1994 | Kumasaka et al. |
| 5,602,899 | A | 2/1997 | Larson |
| 5,604,782 | A | 2/1997 | Cash, Jr. |
| 5,629,969 | A | 5/1997 | Koshishiba |
| 5,657,365 | A | 8/1997 | Yamamoto et al. |
| 5,682,415 | A | 10/1997 | O'Hara |
| 5,729,583 | A * | 3/1998 | Tang ...................... A61B 6/145 378/122 |
| 5,768,339 | A | 6/1998 | O'Hara |
| 5,772,903 | A | 6/1998 | Hirsch |
| 5,825,848 | A | 10/1998 | Virshup |
| 5,832,052 | A | 11/1998 | Hirose et al. |
| 5,857,008 | A | 1/1999 | Reinhold |
| 5,878,110 | A | 3/1999 | Yamamoto et al. |
| 6,108,397 | A | 8/2000 | Cash, Jr. |
| 6,108,398 | A * | 8/2000 | Mazor et al. .................. 378/45 |
| 6,125,167 | A | 9/2000 | Morgan |
| 6,278,764 | B1 | 8/2001 | Barbee, Jr. et al. |
| 6,359,964 | B1 | 3/2002 | Kogan |
| 6,377,660 | B1 | 4/2002 | Ukita |
| 6,381,303 | B1 * | 4/2002 | Vu et al. .......... 378/46 |
| 6,389,100 | B1 | 5/2002 | Verman et al. |
| 6,430,254 | B2 | 8/2002 | Wilkins |
| 6,456,688 | B1 | 9/2002 | Taguchi |
| 6,463,123 | B1 | 10/2002 | Korenev |
| 6,487,272 | B1 | 11/2002 | Kutsuzawa |
| 6,504,902 | B2 | 1/2003 | Iwasaki |
| 6,507,388 | B2 | 1/2003 | Burghoorn |
| 6,553,096 | B1 | 4/2003 | Zhou |
| 6,560,313 | B1 | 5/2003 | Harding |
| 6,560,315 | B1 | 5/2003 | Price |
| 6,707,883 | B1 | 3/2004 | Tiearney, Jr. et al. |
| 6,711,234 | B1 | 3/2004 | Loxley |
| 6,811,612 | B2 | 11/2004 | Gruen et al. |
| 6,815,363 | B2 | 11/2004 | Yun et al. |
| 6,829,327 | B1 | 12/2004 | Chen |
| 6,847,699 | B2 | 1/2005 | Rigali et al. |
| 6,850,598 | B2 | 2/2005 | Fryda et al. |
| 6,870,172 | B1 | 3/2005 | Mankos et al. |
| 6,885,503 | B2 | 4/2005 | Yun |
| 6,914,723 | B2 | 7/2005 | Yun |
| 6,917,472 | B1 | 7/2005 | Yun |
| 6,947,522 | B2 | 9/2005 | Wilson et al. |
| 6,975,703 | B2 | 12/2005 | Wilson |
| 7,003,077 | B2 | 2/2006 | Jen |
| 7,015,467 | B2 | 3/2006 | Maldonado |
| 7,057,187 | B1 | 6/2006 | Yun et al. |
| 7,079,625 | B2 | 7/2006 | Lenz |
| 7,095,822 | B1 | 8/2006 | Yun |
| 7,119,953 | B2 | 10/2006 | Yun |
| 7,130,375 | B1 | 10/2006 | Yun |
| 7,170,969 | B1 | 1/2007 | Yun et al. |
| 7,180,981 | B2 | 2/2007 | Wang |
| 7,183,547 | B2 | 2/2007 | Yun |
| 7,215,736 | B1 | 5/2007 | Wang |
| 7,215,741 | B2 | 5/2007 | Ukita |
| 7,218,700 | B2 | 5/2007 | Huber et al. |
| 7,218,703 | B2 | 5/2007 | Yada |
| 7,221,731 | B2 | 5/2007 | Yada |
| 7,245,696 | B2 | 7/2007 | Yun |
| 7,268,945 | B2 | 9/2007 | Yun |
| 7,286,640 | B2 | 10/2007 | Yun |
| 7,297,959 | B2 | 11/2007 | Yun |
| 7,298,826 | B2 | 11/2007 | Inazuru |
| 7,330,533 | B2 | 2/2008 | Sampayon |
| 7,346,148 | B2 | 3/2008 | Ukita |
| 7,359,487 | B1 | 4/2008 | Newcome |
| 7,365,909 | B2 | 4/2008 | Yun et al. |
| 7,365,918 | B1 | 4/2008 | Yun et al. |
| 7,382,864 | B2 | 6/2008 | Hebert |
| 7,388,942 | B2 | 6/2008 | Wang |
| 7,394,890 | B1 | 7/2008 | Wang |
| 7,400,704 | B1 | 7/2008 | Yun et al. |
| 7,406,151 | B1 * | 7/2008 | Yun .......................... G21K 7/00 378/43 |
| 7,412,024 | B1 | 8/2008 | Yun |
| 7,412,131 | B2 | 8/2008 | Lee |
| 7,414,787 | B2 | 8/2008 | Yun |
| 7,443,953 | B1 * | 10/2008 | Yun et al. ...................... 378/84 |
| 7,499,521 | B2 | 3/2009 | Wang |
| 7,522,707 | B2 | 4/2009 | Steinlage et al. |
| 7,529,343 | B2 | 5/2009 | Safai et al. |
| 7,551,719 | B2 | 6/2009 | Yokhin et al. |
| 7,551,722 | B2 | 6/2009 | Ohshima |
| 7,561,662 | B2 | 7/2009 | Wang |
| 7,583,789 | B1 | 9/2009 | MacDonald |
| 7,601,399 | B2 | 10/2009 | Barnola |
| 7,672,433 | B2 | 3/2010 | Zhong et al. |
| 7,680,243 | B2 | 3/2010 | Yokhin et al. |
| 7,787,588 | B1 | 8/2010 | Yun et al. |
| 7,796,725 | B1 | 9/2010 | Wu et al. |
| 7,800,072 | B2 | 9/2010 | Yun |
| 7,813,475 | B1 | 10/2010 | Wu et al. |
| 7,817,777 | B2 | 10/2010 | Baumann et al. |
| 7,864,426 | B2 | 1/2011 | Yun et al. |
| 7,864,922 | B2 | 1/2011 | Kawabe |
| 7,873,146 | B2 | 1/2011 | Okunuki |
| 7,889,844 | B2 | 2/2011 | Okunuki |
| 7,914,693 | B2 | 3/2011 | Jeong et al. |
| 7,920,676 | B2 | 4/2011 | Yun et al. |
| 7,929,667 | B1 | 4/2011 | Zhuang |

(56) References Cited

U.S. PATENT DOCUMENTS

| | | |
|---|---|---|
| 7,974,379 B1 | 7/2011 | Case |
| 7,991,120 B2 | 8/2011 | Okunuki |
| 8,036,341 B2 | 10/2011 | Lee |
| 8,068,579 B1 | 11/2011 | Yun et al. |
| 8,094,784 B2 | 1/2012 | Morton |
| 8,139,716 B2 | 3/2012 | Okunuki |
| 8,208,603 B2 | 6/2012 | Sato |
| 8,243,884 B2 | 8/2012 | Rödhammer et al. |
| 8,306,184 B2 | 11/2012 | Chang |
| 8,353,628 B1 | 1/2013 | Yun et al. |
| 8,360,640 B2 | 1/2013 | Reinhold |
| 8,406,378 B2 | 3/2013 | Wang |
| 8,416,920 B2 | 4/2013 | Okumura et al. |
| 8,422,633 B2 | 4/2013 | Lantz |
| 8,422,637 B2 | 4/2013 | Okunuki et al. |
| 8,509,386 B2 | 8/2013 | Lee |
| 8,520,803 B2 | 8/2013 | Behling |
| 8,526,575 B1 | 9/2013 | Lyon |
| 8,553,843 B2 | 10/2013 | Drory |
| 8,559,597 B2 | 10/2013 | Chen et al. |
| 8,602,648 B1 | 12/2013 | Jacobsen |
| 8,666,024 B2 | 3/2014 | Okunuki et al. |
| 8,699,667 B2 | 4/2014 | Steinlage et al. |
| 8,735,844 B1 | 5/2014 | Khaykovich et al. |
| 8,737,565 B1 | 5/2014 | Lyon |
| 8,744,048 B2 | 6/2014 | Lee et al. |
| 8,831,175 B2 | 9/2014 | Silver et al. |
| 8,831,179 B2 | 9/2014 | Adler |
| 8,861,682 B2 | 10/2014 | Okunuki |
| 8,995,622 B2 | 3/2015 | Adler |
| 9,008,278 B2 | 4/2015 | Lee et al. |
| 9,016,943 B2 | 4/2015 | Jacobsen |
| 9,020,101 B2 | 4/2015 | Omote et al. |
| 9,129,715 B2 | 9/2015 | Adler et al. |
| 2001/0006413 A1 | 7/2001 | Burghoorn |
| 2003/0142790 A1 | 7/2003 | Zhou |
| 2004/0120463 A1 | 6/2004 | Wilson et al. |
| 2004/0140432 A1 | 7/2004 | Maldonado |
| 2005/0074094 A1 | 4/2005 | Jen |
| 2005/0123097 A1 | 6/2005 | Wang |
| 2005/0163284 A1 | 7/2005 | Inazuru |
| 2005/0282300 A1 | 12/2005 | Yun et al. |
| 2007/0071174 A1 | 3/2007 | Hebert |
| 2007/0108387 A1 | 5/2007 | Yun et al. |
| 2007/0110217 A1 | 5/2007 | Ukita |
| 2007/0248215 A1* | 10/2007 | Ohshima et al. ............. 378/143 |
| 2008/0089484 A1 | 4/2008 | Reinhold |
| 2008/0094694 A1 | 4/2008 | Yun et al. |
| 2008/0159707 A1 | 7/2008 | Lee |
| 2008/0170662 A1 | 7/2008 | Reinhold |
| 2008/0170668 A1 | 7/2008 | Kruit et al. |
| 2008/0181363 A1 | 7/2008 | Fenter |
| 2008/0240344 A1 | 10/2008 | Reinhold |
| 2008/0273662 A1* | 11/2008 | Yun et al. ...................... 378/74 |
| 2009/0154640 A1 | 6/2009 | Baumann et al. |
| 2009/0316860 A1 | 12/2009 | Okunuki et al. |
| 2010/0040202 A1 | 2/2010 | Lee |
| 2010/0141151 A1 | 6/2010 | Reinhold |
| 2010/0272239 A1 | 10/2010 | Lantz |
| 2010/0284513 A1 | 11/2010 | Kawabe |
| 2011/0026680 A1* | 2/2011 | Sato ............................ 378/119 |
| 2011/0058655 A1 | 3/2011 | Okumura et al. |
| 2011/0135066 A1 | 6/2011 | Behling |
| 2012/0163547 A1 | 6/2012 | Lee et al. |
| 2012/0269323 A1 | 10/2012 | Adler |
| 2012/0269324 A1 | 10/2012 | Adler |
| 2012/0269325 A1 | 10/2012 | Adler |
| 2012/0269326 A1 | 10/2012 | Adler |
| 2013/0195246 A1* | 8/2013 | Tamura et al. ................. 378/62 |
| 2013/0259207 A1 | 10/2013 | Omote |
| 2013/0308754 A1 | 11/2013 | Yamazaki |
| 2014/0037052 A1 | 2/2014 | Adler |
| 2014/0064445 A1 | 3/2014 | Adler |
| 2014/0072104 A1 | 3/2014 | Jacobsen |
| 2014/0079188 A1 | 3/2014 | Hesselink et al. |
| 2014/0105363 A1 | 4/2014 | Chen et al. |
| 2014/0177800 A1 | 6/2014 | Sato et al. |
| 2014/0185778 A1 | 7/2014 | Lee et al. |
| 2014/0211919 A1 | 7/2014 | Ogura |
| 2014/0369469 A1 | 12/2014 | Ogura et al. |
| 2015/0030127 A1 | 1/2015 | Aoki |
| 2015/0043713 A1 | 2/2015 | Chen |

FOREIGN PATENT DOCUMENTS

| | | |
|---|---|---|
| EP | 1028451 A1 | 8/2000 |
| JP | H07-056000 A | 3/1995 |
| JP | 2000-306533 A | 11/2000 |
| JP | 2007-265981 A | 10/2007 |
| JP | 2007-311185 A | 11/2007 |
| JP | 2013-157269 A | 8/2013 |
| JP | 2013-160637 A | 8/2013 |
| JP | 2013-239317 A | 11/2013 |
| JP | 2015-047306 A | 3/2015 |
| JP | 2015-077289 A | 4/2015 |
| WO | 95/06952 A1 | 3/1995 |
| WO | 98/11592 A1 | 3/1998 |
| WO | 02/39792 A2 | 5/2002 |
| WO | 03/081631 A2 | 10/2003 |
| WO | 2005/109969 A2 | 11/2005 |
| WO | 2006/096052 A2 | 9/2006 |
| WO | 2009/098027 A1 | 8/2009 |
| WO | 2013/118593 A1 | 8/2013 |
| WO | 2013/168468 A1 | 11/2013 |

OTHER PUBLICATIONS

Leenaers et al., Application of Glancing Incidence X-ray Analysis, 1997, X-ray Spectrometry, vol. 26, pp. 115-121.*

Oxford Instruments Inc.., Series 5000 Model XTF5011 X-ray Tube information, Jun. 1998, 3 pages.*

Abuillan et al., Quantitative determination of the lateral density and intermolecular correlation between proteins anchored on the membrane surfaces using grazing incidence small-angle X-ray scattering and grazing incidence X-ray fluorescence, Nov. 28, 2012, The Journal of Chemical Physics, vol. 137, pp. 204907-1 to 204907-8.*

Yakimchuk et al., Ellipsoidal Concentrators for Laboratory X-ray Sources: Analytical approaches for Optimization, Mar. 22, 2013, Crystallography Reports, vol. 58, No. 2, pp. 355-364.*

Yasuo Udagawa, "An Introduction to In-House EXAFS Facilities" The Rigaku Journal, vol. 6 (1) (1989), pp. 20-27.

C. Malgrange, "X-ray Optics for Synchrotron Radiation" ACTA Physica Polinica A, vol. 82(1) (1992), pp. 13-32.

Yasuo Udagawa, "An Introduction to X-ray Absorption Fine Structure", The Rigaku Journal, vol. 11(2) (1994), pp. 30-39.

Alfred Q.R. Baron et al., "A compact optical design for Bragg reflections near backscattering", J. Synchrotron Rad. vol. 8 (2001), pp. 1127-1130.

P. Lechner et al., "Silicon drift detectors for high count rate X-ray spectroscopy at room temperature", Nuclear Instruments and Methods, vol. 458A, (2001), pp. 281-287.

Matthew Newville, "Fundamentals of XAFS" (Univ. of Chicago, Chicago, IL, Jul. 23, 2004).

Kouichi Tsuji, Jasna Injuk & Rene Van Grieken, "X-Ray Spectrometry: Recent Technological Advances" (John Wiley & Sons Ltd, Chichester, West Sussex, UK, 2004), Chapters 1-7.

J. A. Maj et al. "Etching methods for improving surface imperfections of diamonds used for x-ray monochromators" Adv. X-ray Anal. vol. 48 (2005), pp. 176-182.

Tirandai Hemraj-Benny et al., "Near-Edge X-ray Absorption Fine Structure Spectroscopy as a Tool for Investigating Nanomaterials", Small vol. 2(1), (2006) pp. 26-35.

Markus Scholz, "X-ray Tubes and Monochromators", Technical Workshop EPIV, Universität Würzburg (2007); 41 slides, available at <http://www.physik.uni-wuerzburg.de/EP4/teaching/WS2007_08/technikseminar/xraytubesws0708.pdf>.

J. Hrdý and J. Hrdá, "Diffractive-Refractive Optics: X-ray Crystal Monochromators with Profiled Diffracting Surfaces", Ch. 26. of

(56) References Cited

OTHER PUBLICATIONS

"Modern Developments in X-Ray and Neutron Optics", A. Erko et al., eds. (Springer, Berlin Heidelberg New York, 2008).
T. Matsushita, "X-ray monochromators", Slide Presentation from Photon Factory, Tsukuba, Japan, 70 slides, (Cheiron School 2009, SPring-8, Japan, Nov. 2009) available at < http://cheiron2009.spring8.or.jp/images/PDF/Lecture/X-ray_Monochromator_T_Matsushita.pdf >.
Mauro Rovezzi, "Study of the local order around magnetic impurities in semiconductors for spintronics", PhD dissertation, Condensed Matter. Université Joseph-Fourier—Grenoble I, 2009. English <tel-00442852>.
Jens Als-Nielsen & Des McMorrow "Photoelectric Absorption", Ch. 7 of "Elements of Modern X-ray Physics, Second Edition", (John Wiley & Sons Ltd, Chichester, West Sussex, UK, 2011).
David Gibson & Walter Gibson, "Polycpillary Optics: An Enabling Technology for New Applications", Advances in X-ray Analysis vol. 45 (2002), pp. 286-297.
C. A. MacDonald, S. M. Owens and W. M. Gibson, "Polycapillary X-ray optics for microdiffraction", J. Appl. Cryst. vol. 32 (1999), pp. 160-167.
Paul J. Shields et al., "Overview of polycapillary X-ray optics", Powder Diffraction vol. 17(2) (Jun. 2002), pp. 70-80.
"Series 5000 Packaged X-ray tubes", Product Technical Data Sheet DS006 Rev. G, X-Ray Technologies Inc. (Oxford Instruments), Scotts Valley, CA (no date).
W.C. Röntgen, Ueber eine neue Art von Strahlen (Würzburg Verlag, Würzburg, Germany, 1896) also, in English, "On a New Kind of Rays," Nature vol. 53 (Jan. 23, 1896), pp. 274-276.
N. Langhoff & A. Simionovici, "X-ray Sources", Ch. 2 of "Handbook of Practical X-Ray Fluorescence Analysis", B. Beckhoff et al., eds. (Springer, Berlin Heidelberg New York, 2006), pp. 33-82.
Jens Als-Nielsen & Des McMorrow "X-rays and their interaction with matter", and "Sources", Ch.1 & 2 of "Elements of Modern X-ray Physics, Second Edition" (John Wiley & Sons Ltd, Chichester, West Sussex, UK, 2011), pp. 1-67.
P.J. Potts, "Electron Probe Microanalysis", Ch. 10 of "A Handbook of Silicate Rock Analysis" (Springer Science + Business Media, New York, 1987), pp. 326-382 (equation quoted from p. 336).
J. G. Chervenak & A. Liuzzi, "Experimental thick-target bremsstrahlung spectra from electrons in the range 10 to 30 keV", Phys. Rev. A vol. 12 (1975), pp. 26-33.
P.D. Prewitt et al., "FIB Repair of 5X Reticles and Effects on IC Quality", in Integrated Circuit Metrology, Inspection, and Process Control VII, Proc. SPIE vol. 1926 (1993), pp. 517-526.
P.D. Prewitt et al., "Gallium Staining in FIB Repair of Photomasks", Microelectronic Engineering vol. 21 (1993), pp. 191-196.
P.D. Prewitt and G.M. Sundaram,"Focused ion beam repair: staining of photomasks and reticles" J. Phys. D Appl. Phys. vol. 26 (1993), pp. 1135-1137.
Guifu Ding et al., "Reactive Ion Etching of CVD Diamond Films for MEMS Applications", in Micromachining and Microfabrication, Proc. SPIE vol. 4230 (2000) pp. 224-230.
Qiaoqin Yang et al., "Analysis of Intrinsic Stress in Diamond Films by X-ray Diffraction", in Advances in X-ray Analysis, vol. 43 (2000) pp. 151-156.
X.D. Wang et al., "Precise patterning of diamond films for MEMS application" Journal of Materials Processing Technology vol. 127 (2002), pp. 230-233.
Heinz-Dieter Nuhn, "From storage rings to free electron lasers for hard x-rays", J. Phys.: Condens. Matter vol. 16 (2004), pp. S3413-S34121.
Shigehiko Yamamoto, "Fundamental physics of vacuum electron sources", Reports on Progress in Physics vol. 69, (2006), pp. 181-232.
"Diamond", Section 10.4.2 of Christian A. Zorman and Mehran Mehregany, "Material Aspects of Micro-Nanoelectromechanical Systems", Chapter 10 of Springer Handbook of Nanotechnology, 2nd Ed., Barat Bushan, ed. (Springer Science + Business Media, Inc., New York, 2007) pp. 312-314.
M. Otendal T. Tuohimaa, U. Vogt & H.M. Hertz, "A 9 keV electron-impact liquid-gallium-jet x-ray source", Rev. Sci. Instrum. vol. 79 (2008): 016102.
Aamir Ihsan, Sung Hwan Heo & Sung Oh Cho , "A microfocus X-ray tube based on a microstructured X-ray target", Nuclear Instruments and Methods in Physics Research B vol. 267 (2009), pp. 3566-3573.
Genta Sato et al., "Two-dimensional gratings-based phase-contrast imaging using a conventional x-ray tube", Opt. Lett. vol. 36(18) (2011), pp. 3551-3553.
N. Morimoto et al., "Development of multiline embedded X-ray targets for X-ray phase contrast imaging", in XTOP 2012 Book of Abstracts (Ioffe Physical-Technical Institute of the Russian Academy of Sciences, St. Petersburg, Russia, 2012), pp. 74-75.
D. Gonzales, B. Cavness & S. Williams, "Angular distribution of thick-target bremsstrahlung produced by electrons with initial energies ranging from 10 to 20 keV incident on Ag", Phys. Rev. A vol. 84 (2011): 052726.
D. Gonzales & S. Williams, "Angular Distribution of Bremsstrahlung Produced by 10-Kev and 20 Kev Electrons Incident on a Thick Au Target", in Application of Accelerators in Research and Industry, AIP Conf. Proc. 1525 (2013), pp. 114-117.
Jicheng Zhang et al., "Fabrication of Diamond Microstructures by Using Dry and Wet Etching Methods", Plasma Science and Technology vol. 15(6) (Jun. 2013), pp. 552-554.
Takayoshi Shimura et al., "Hard x-ray phase contrast imaging using a tabletop Talbot-Lau interferometer with multiline embedded x-ray targets", Opt. Lett. vol. 38(2) (2013) pp. 157-159.
Alireza Nojeh, "Carbon Nanotube Electron Sources: From Electron Beams to Energy Conversion and Optophononics", ISRN Nanomaterials vol. 2014 (2014): 879827.
Paul Kirkpatrick & A.V. Baez, "Formation of Optical Images by X-Rays" J. Opt. Soc. Am. vol. 38 (Sep. 1948), pp. 766-774.
Hans Wolter, "Spiegelsysteme streifenden Einfalls als abbildende Optiken für Röntgenstrahlen" [Grazing-Incidence Reflector Systems as Imaging Optics for X-rays] Annalen der Physik vol. 445, Issue 1-2 (1952), pp. 94-114.
Janos Kirz, "Phase zone plates for x rays and the extreme uv" J. Opt. Soc. Am. vol. 64 (Mar. 1974) pp. 301-309.
Troy W. Barbee Jr. "Multilayers for x-ray optics" Opt. Eng. vol. 25 (Aug. 1986) pp. 898-915.
Malcolm R. Howells, "Mirrors for Synchrotron-Radiation Beamlines", Publication LBL-34750 (Larrence Berkeley Laboratory, Berkeley, CA, Sep. 1993).
David X. Balaic & Keith A. Nugent, "X-ray optics of tapered capillaries" Appl. Opt. vol. 34 (Nov. 1995), pp. 7263-7272.
Muradin A. Kumakhov, "X-ray Capillary Optics. History of Development and Present Status" in Kumakhov Optics and Application, Proc. SPIE vol. 4155 (2000), pp. 2-12.
Carolyn A. Macdonald & Walter M. Gibson, "An Introduction to X-ray and Neutron Optics", Ch. 19 of "Handbook of Optics vol. III, 2nd Ed." (McGraw Hill, New York, 2001).
B. Lengeler, C. Schroer, J. Tümmler, B. Benner, A. Snigirev & I. Snigireva, "Refractive X-ray Optics", Ch. 20 of "Handbook of Optics vol. III, 2nd Ed." (McGraw Hill, New York, 2001).
Malcolm R. Howells, "Gratings and Monochromators in the VUV and Soft X-ray Spectral Region" Ch. 21 of "Handbook of Optics vol. III, 2nd Ed." (McGraw Hill, New York, 2001).
Peter Siddons, "Crystal Monochromators and Bent Crystals" Ch. 22 of "Handbook of Optics vol. III, 2nd Ed." (McGraw Hill, New York, 2001).
Alan Michette, "Zone and Phase Plates, Bragg-Fresnel Optics" Ch. 23 of "Handbook of Optics vol. III, 2nd Ed." (McGraw Hill, New York, 2001).
Eberhard Spiller, "Multilayers" Ch. 24 of "Handbook of Optics vol. III, 2nd Ed." (McGraw Hill, New York, 2001).
Qun Shen, "Polarizing Crystal Optics" Ch. 25 of "Handbook of Optics vol. III, 2nd Ed." (McGraw Hill, New York, 2001).
Andreas Freund, "Mirrors for Synchrotroin Beamlines" Ch. 26 of "Handbook of Optics vol. III, 2nd Ed." (McGraw Hill, New York, 2001).
F. Cerrina, "The Schwarzschild Objective" Ch. 27 of "Handbook of Optics vol. III, 2nd Ed." (McGraw Hill, New York, 2001).

(56) References Cited

OTHER PUBLICATIONS

Marshall K. Joy, "Astronomical X-ray Optics" Ch. 28 of "Handbook of Optics vol. III, 2nd Ed." (McGraw Hill, New York, 2001).
Donald H. Bilderback & Edward D. Franco, "Single Capillaries" Ch. 29 of "Handbook of Optics vol. III, 2nd Ed." (McGraw Hill, New York, 2001).
Carolyn A. Macdonald & Walter M. Gibson, "Polycapillary and Multichannel Plate X-Ray Optics" Ch. 30 of "Handbook of Optics vol. III, 2nd Ed." (McGraw Hill, New York, 2001).
M. Yanagihara et al., "X-Ray Optics", Ch. 3 of "X-ray Spectrometry: Recent Technological Advances", K. Tsuji et al. eds. (John Wiley & Sons, Ltd. Chichester, West Sussex, UK, 2004), pp. 63-131.
A. Erko et al., "X-ray Optics", Ch. 3 of "Handbook of Practical X-Ray Fluorescence Analysis", B. Beckhoff et al., eds. (Springer, Berlin, Germany, 2006), pp. 85-198.
Barry Lai, "X-Ray Microfocusing Optics", Slide Presentation from Argonne National Laboratory, 71 slides, Cheiron Summer School 2007, available at: < http://cheiron2007.spring8.or.jp/pdf/Lai.pdf >.
Sterling W. Cornaby et al., "Design of Single-Bounce Monocapillary X-ray Optics", in Advances in X-ray Analysis: Proceedings of the 55th Annual Conference on Applications of X-ray Analysis, vol. 50 (International Centre for Diffraction Data (ICDD), 2007), pp. 194-200.
A. Snigirev & I. Snigireva, "Hard X-Ray Microoptics", Ch. 17 of "Modern Developments in X-Ray and Neutron Optics", A. Erko et al., eds (Springer, Berlin, Germany, 2008), pp. 255-285.
A. Bjeoumikhov & S. Bjeoumikhova, "Capillary Optics for X-Rays", Ch. 18 of "Modern Developments in X-Ray and Neutron Optics", A. Erko et al., eds (Springer, Berlin, Germany, 2008), pp. 287-306.
S. Lagomarsino et al., "Reflective Optical Arrays", Ch. 19 of "Modern Developments in X-Ray and Neutron Optics", A. Erko et al., eds (Springer, Berlin, Germany, 2008), pp. 307-317.
Sterling W. Cornaby, "The Handbook of X-ray Single-Bounce Monocapillary Optics, Including Optical Design and Synchrotron Applications" (PhD Dissertation, Cornell University, Ithaca, NY,May 2008).
Xianghui Zeng et al., "Ellipsoidal and parabolic glass capillaries as condensers for x-ray microscopes", Appl. Opt. vol. 47 (May 2008), pp. 2376-2381.
"Optics and Detectors", Section 4 of X-Ray Data Booklet, 3rd Ed., A.C. Thompson ed. (Lawrence Berkeley Nat'l Lab. Berkeley, CA, 2009). Available at < http://xdb.lbl.gov/ >.
P. Guttmann et al., "Ellipsoidal capillary as condenser for the BESSY full-field x-ray microscope", J. Phys. Conf. Ser. vol. 186 (2009): 012064.
Sterling W. Cornaby et al., "Advances in X-ray Microfocusing with Monocapillary Optics at CHESS" CHESS News Magazine (2009), pp. 63-66.
T. Matsushita, "Mirrors and Multilayers", Slide Presentation from Photon Factory, Tsukuba, Japan, 65 slides, (Cheiron School 2009, SPring-8, Japan, Nov. 2009) available at: < http://cheiron2009.spring8.or.jp/images/PDF/Lecture/Mirror_and_Multilayer_T_Matsushita.pdf >.
X. Zeng et. al., "Glass Monocapillary X-ray Optics and Their Applications in X-Ray Microscopy", in X-ray Optics and Microanalysis: Proceedings of the 20th International Congress, AIP Conf. Proc. vol. 1221, (2010), pp. 41-47.
Roger Falcone et al., "New directions in X-ray microscopy", contemporary Physics vol. 52, No. 4 (Jul.-Aug. 2010), pp. 293-318.
Carolyn A. Macdonald, "Focusing Polycapillary Optics and Their Applications", X-Ray Optics and Instrumentation vol. 2010, (Oct. 2010): 867049.
Jens Als-Nielsen & Des McMorrow "Refraction and reflection from interfaces", Ch. 3 of "Elements of Modern X-ray Physics, Second Edition", (John Wiley & Sons Ltd, Chichester, West Sussex, UK, 2011), pp. 69-112.
"X-ray Optics for BES Light Source Facilities", Report of the Basic Energy Sciences Workshop on X-ray Optics for BES Light Source Facilities, D. Mills & H. Padmore, Co-Chairs, (U.S. Dept. of Energy, Office of Science, Potomac, MD, Mar. 2013). < http://science.energy.gov/~/media/bes/pdf/reports/files/BES_XRay_Optics_rpt.pdf >.
Yoshio Suzuki et al., "Hard X-ray Imaging Microscopy using X-ray Guide Tube as Beam Condenser for Field Illumination" J. Phys.: Conf. Ser. vol. 463 (2013): 012028.

\* cited by examiner

X-RAY SURFACE ANALYSIS AND MEASUREMENT APPARATUS

CROSS-REFERENCE TO RELATED APPLICATIONS

This patent application claims the benefit of U.S. Provisional Patent Application Nos. 61/946,475 and 61/946,527, both filed on Feb. 28, 2014; 62/008,856, filed Jun. 6, 2014; 62/086,132, filed Dec. 1, 2014, and 62/117,062, filed Feb. 17, 2015, all of which are incorporated herein by reference in their entirety.

FIELD OF THE INVENTION

The present application presents an x-ray analysis and measurement apparatus for analysis, quantification of chemical composition, structural determination, measurements and metrology of a sample with a flat surface or for samples such as fine particles or liquid that are deposited on a flat surface of a substrate. The x-ray techniques may include total reflection x-ray fluorescence analysis (TXRF), grazing incidence x-ray diffraction (GIXRD), grazing incidence diffraction (GID), grazing incidence x-ray small angle scattering (GISAXS), and x-ray reflectivity (XRR), singularly or in combination.

BACKGROUND OF THE INVENTION

Total reflection x-ray analysis (TXRF), x-ray reflectometry (XRR), grazing incidence x-ray diffraction (GIXRD), grazing incidence diffraction (GID), and grazing incidence small angle x-ray scattering (GISAXS), are well-established x-ray surface analysis and measurement techniques [see, for example, R. Klockenkämper and A. von Bohlen, *Total Reflection X-ray Fluorescence Analysis and Related Methods* 2nd Ed. (J. Wiley and Sons, 2015); R. Fernandez-Ruiz, "TXRF Spectrometry as a Powerful Tool for the Study of Metallic Traces in Biological Systems" *Development in Analytical Chemistry* Vol. 1 2014; M. Birkholz, "Chapter 4: Grazing Incidence Configurations", in *Thin Film Analysis by X-ray Scattering* (Wiley-VCH Verlag GmbH & Co. KGaA, Weinheim, Germany, 2005); and G. Renaud et al., "Probing surface and interface morphology with Grazing Incidence Small Angle X-ray Scattering" *Surface Science Reports* vol. 64:8 (2009), pp. 255-380]. These grazing incidence techniques utilize an X-ray beam incident upon a sample surface with an incidence angle smaller than the critical angle for total reflection of the surface material at the incident x-ray energy. Under this condition, the incident x-rays penetrate only a short distance into the surface, typically less than 20 nm, resulting the surface sensitivity of the techniques.

TXRF provides highly sensitive chemical composition and concentration analysis and quantification of a thin surface layer (<20 nm) of a sample with a flat surface or a sample (e.g. liquid or fine particles) on top of an optically flat substrate by measuring the x-rays produced by the sample under x-ray excitation. It may also be used to determine the thickness of a thin film on top of an optically flat substrate.

XRR measures the intensity of x-rays undergoing specular reflection from a surface at various angles of incidence to obtain density, thickness, and roughness profiles of surface layers and thin films.

GIXRD is useful for crystalline structural determination of a thin surface layer of a sample with a flat surface by measuring diffraction patterns resulting from an x-ray beam at a grazing incidence angle. This is typically used with flat surfaces. GID records the diffraction pattern at a grazing exit angle.

GISAXS is useful to characterize structures (typically with dimensions on a nanometer scale) of a thin surface layer of a sample as well as inner electron density fluctuations of the deposited material by measuring the scattering signal that results from an x-ray beam of grazing incidence.

For scientific studies of materials that need high brightness x-rays, high brightness synchrotrons or free-electron lasers have been used with great success. However, these facilities are large, often occupying acres of land, and expensive to operate, and obtaining beamtime can take months of waiting. They are impractical for conventional laboratory use.

Until now, laboratory application of the grazing incidence x-ray techniques described above have relied on conventional laboratory x-ray sources that use an extended solid metal anode (such as copper) and have relatively low brightness and limited choice of x-ray spectra of the incident x-ray beam, due to limitation of the x-ray target anode materials with suitable thermal, mechanical, and chemical properties that are required to ensure continuous operation of the x-ray target, typically preventing the anode target from melting, as disclosed in U.S. Pat. Nos. 5,249,216 and 6,829,327, whose disclosures are incorporated herein by reference in their entirety, have disclosed TXRF system designs using existing laboratory x-ray sources.

U.S. Pat. No. 7,929,667, also incorporated herein by reference in its entirety, describes the use of an x-ray source using a liquid metal jet anode to circumvent the thermal limitations of conventional x-ray sources for x-ray metrology applications. However, to achieve the desired benefit, the metal jet needs to be in liquid form and have sufficiently high speed and low vapor pressure, among other challenging requirements. The major limitation of this type of x-ray source is that only an extremely limited number of metals are in liquid form at reasonable temperatures, i.e., below 200 centigrade. Consequently, the choice of x-ray characteristic lines for monochromatic x-ray beam illumination is extremely limited.

To make substantial performance improvements to grazing incidence x-ray techniques, singularly or in combination, there is need of an x-ray apparatus comprising a high brightness laboratory x-ray source, preferably providing flexibility in choice of anode material to produce a range of x-ray energies. Additionally, among these techniques, there is also continued demand for reducing (improving) absolute and/or relative trace element detection limit in liquids and solutions, especially for low atomic number elements (e.g. boron (B), carbon (C), oxygen (O), fluorine (F), sodium (Na), aluminum (Al), and sulfur (S)), improving throughput, quantitative elemental composition analysis accuracy, higher spatial resolution for small spot analysis or mapping/imaging of elemental composition as well as higher sensitivity and performance in determining crystallographic phases and/or texture, measurement of thin film thickness, semiconductor metrology, and measurement of impurities and contamination on silicon surfaces in semiconductor manufacturing.

BRIEF SUMMARY OF THE INVENTION

The present invention discloses an x-ray surface analysis and characterization apparatus that comprises a novel x-ray source using the linear accumulating of x-rays that provides high x-ray brightness and a wide choice of x-ray energy. The linear accumulation x-ray source comprises two or more sub-sources of x-rays, with each sub-source having predetermined x-ray spectral characteristics, with the sub-sources separated physically from each other by predetermined spatial intervals and aligned with each other along a predetermined axis to allow accumulation of x-rays along that axis, thereby increasing brightness. The x-ray sub-sources produce x-rays by electron bombardment of a target, and the linear accumulation of x-rays from the multiple origins leads to greater x-ray brightness.

In some embodiments, the x-ray sub-sources may be a single microstructure, or comprise of one or more embedded multi-microstructures, each of which comprise an x-ray generating material selected for x-ray generating properties, such as spectral characteristic and x-ray production efficiency. The microstructures of x-ray generating material may have at least one dimension less than 10 micrometers, embedded in a substrate of low Z material with high thermal conductivity.

A significant advantage to some embodiments is that the high x-ray brightness from the linearly accumulating source results in greatly improved throughput and higher sensitivity for the above mentioned grazing incidence x-ray techniques, which is particularly important for industrial applications such as semiconductor metrology. Furthermore, the higher brightness combined with a wider range of characteristic x-rays can improve elemental and analytical sensitivity for TXRF and extend the analytical performance capabilities of XRR, TXRF, GIXRD, GID, and GISAXS.

Some embodiments additionally comprise an x-ray optical train that is configured to collect and collimate or focus x-rays along the predetermined axis to produce an x-ray beam with predetermined beam properties, such as the beam profile, intensity cross section, or angular composition, as well as predetermined spectral properties. In some embodiments, the x-ray optical train comprises at least one x-ray mirror optic with an axially symmetric reflecting surface of a predetermined surface profile, selected from paraboloids, ellipsoids, or type I Wolter optics. Additionally, it may include one or more spectral filter(s) or monochromator(s) to narrow the spectral band of the x-ray beam. Furthermore, some embodiments comprise at least one absorbing x-ray collimator, such as an aperture or slit, to collimate the angular convergence of the x-ray beam or the incident x-ray spot upon the sample. The x-ray optic is positioned such that the x-ray beam is directed to be incident at a grazing angle upon the flat surface of a sample to be analyzed.

Additional advantages may be provided in some embodiments of the invention by using an axially symmetric x-ray optic with a large numerical aperture, producing a higher brightness x-ray beam incident upon the sample. Additional advantages may be provided in some embodiments of the invention by using optics of small point spread function and using a flat crystal monochromators within the optical train to provide higher spatial resolution and analytical sensitivity.

At least one detector receives x-rays from the sample in response to the interaction of the incident x-ray beam with the sample, and produces signals indicative of properties of the sample. The x-ray signals from the sample might include characteristic fluorescent x-rays resulting from absorption of the incident x-rays or diffracted, scattered, and reflected x-rays. An electromechanical system controls the source, the components of the optical train, positioning the sample with respect to the incident x-ray beam, and the detector, acquires data, and determines the properties of the sample based on the x-ray signals at least in part, singularly or in combination.

In various embodiments, the x-ray surface analysis and measurement apparatus is configured to perform TXRF, XRR, GIXRD, GID, and GISAXS, singularly, sequentially, or simultaneously in combination of a subset or all of the above techniques. Example applications include analysis of material contamination of semiconductor wafers, elemental composition analysis and thin film thickness measurement during semiconductor device manufacturing processes, such as dielectric materials, copper diffusion barriers, composition analysis and size and size distribution characterization of nanoparticles deposited on a flat surface, trace element detection and analysis in solutions and solid (with digestion) in forensics, pharmaceuticals, food, environmental samples, and biological tissue.

Figure 1:
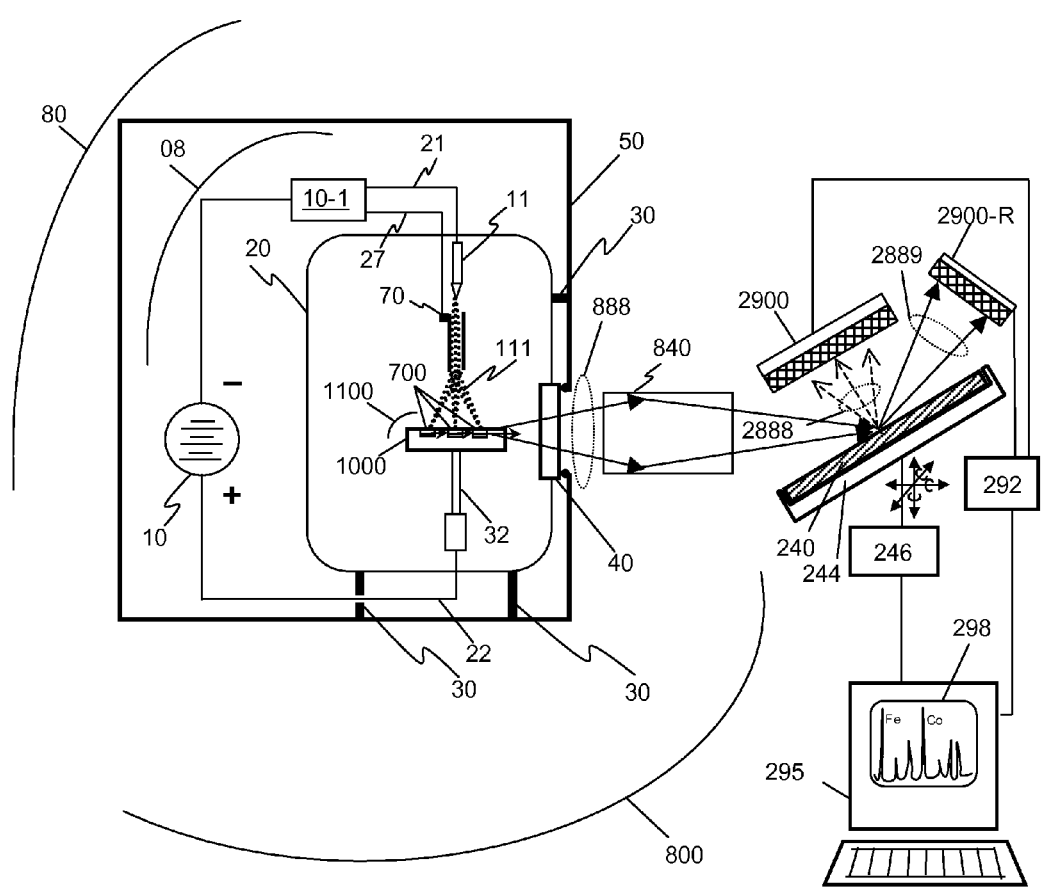
FIG. 1 schematically illustrates a surface x-ray analysis and measurement apparatus using a linear accumulation x-ray source according to the invention.

Note: The accompanying drawings, which are incorporated in and constitute a part of the specification, illustrate exemplary embodiments, features, and aspects of the invention and, together with the description, serve to explain the principles of the invention. The drawings are not necessarily to scale; emphasis has instead been placed upon illustrating the principles of the invention.

DETAILED DESCRIPTIONS OF EMBODIMENTS OF THE INVENTION

For all of the surface x-ray techniques mentioned above, the x-ray flux F of the x-ray beam incident on the sample surface is an important parameter and is equal to the product of the x-ray beam brightness $B_s$ at the sample (defined as number of x-rays per unit area and per unit solid angle illuminating the sample), the cross sectional area A' of the incident beam at the sample point, and the convergence angles: $\Delta\theta$ in the scattering plane which contains incident and reflected x-ray beam, and $\omega$ in the out-plane which is perpendicular to the reflection plane:

$$F = B_s A' \Delta\theta^* \omega \quad [\text{Eqn. 1}]$$

The x-ray beam brightness $B_s$ at the sample is typically smaller than the x-ray source brightness (B) because the inherent low focusing efficiency and aberrations of the x-ray optical train lead to blurring and therefore an increase in the effective x-ray source size. $B_s$ and B are approximately related by:

$$B_s = B\rho \frac{s^2}{s^2 + [M\delta/(M+1)]^2} \quad [\text{Eqn. 2}]$$

where $\rho$ is the total focusing efficiency of the all the optical components of the x-ray optical train from the source to the sample, s is the diameter of the source size (assumed to be of a circular shape), $\delta$ the full width half maximum (FWHM) of the point spread function (PSF) of the x-ray optical train, and M the image magnification of the x-ray optical train. Note that M is equal to infinity when the source is located at a focus of the x-ray optical train.

Eqns. 1 and 2 show that for given incident beam cross sectional area A' and beam angular convergence $\Delta\theta$, to increase F, it is desirable to have a high brightness x-ray source B, an x-ray optical train with high efficiency p, and a FWHM of the PSF optical train $\delta$ smaller than the source size s, and a large out-of-plane angle $\omega$ which is enabled by using an optic that has a large solid angle of collection along the out-of-plane direction.

Various embodiments of the present invention obtain a large F by increasing B with a bright linear accumulation x-ray source, and enable large $B_s$, $\rho$, and $\omega$ values with a high performance x-ray optical train comprising an x-ray mirror optic. The value of $\Delta\theta$ must be constrained to be what is suitable for the grazing incidence surface x-ray techniques (less than the critical angle of reflection of the sample or substrate at the incident x-ray energy of interest) and can be achieved by using additional x-ray aperture(s) or slit(s). The maximum value of $\Delta\theta$ is set to be less than the critical angle of reflection of the substrate at the x-ray energy of the incident x-ray beam, which is inversely proportional to the x-ray energy E and the square root of the mass density of the sample or substrate, which are well-known values, some of which may be found through websites and references such as the X-ray Optics Calculator at:
purple.ipmt-hpm.ac.ru/xcalc/xcalc_mysql/ref_index.php.

By using a two dimensional X-Y Cartesian coordinate system in the sample surface, with the X axis defined as being parallel to the x-ray beam and the scattering plane (containing the incident and reflected x-ray beam axis) and the Y axis perpendicular to the X axis, the area $A=A'/\sin(\theta)$ of the beam footprint on the sample placed at the focus of the focused x-ray beam can be expressed by:

$$A = L_y \frac{L_x}{\sin\theta} \quad [\text{Eqn. 3}]$$

where $L_x$ and $L_y$ are the cross sectional beam size in the X and Y directions, respectively, and $\theta$ the mean grazing incidence angle.

$L_x$ and $L_y$ are in turn given b $$L_i = \sqrt{\left(\frac{M S_i}{M+1}\right)^2 + \delta^2} \quad [\text{Eqn. 4}]$$

where i may correspond to either X or Y, M is the magnification of the x-ray optical train, $S_i$ the full width half maximum (FWHM) size of the linear accumulation x-ray source in the respective direction, and $\delta$ the full width half maximum (FWHM) of the point spread function (PSF) of the x-ray optical train.

For many applications, a small area A is required to obtain small spot analysis or perform high resolution spatial mapping over a large area, such as mapping surface contaminants over a wafer in semiconductor manufacturing. Various embodiments of the present invention obtains a small A by using a linear accumulation x-ray source with a small source size $S_i$, an x-ray optical train with a small FWHM point spread function $\delta$, and/or a small magnification factor M.

Additionally, in some embodiments it is preferred to use x-rays of lower incident x-ray energies, as it can increase the critical angle $\theta$ and thus the convergence angles $\Delta\theta$ and $\omega$ to obtain a small foot print dimension A on the sample in the scattering plane (due to the $1/\sin(\theta)$ factor) and to increase F. Furthermore, specific elements, especially low Z elements, have much higher x-ray fluorescence cross-sections at lower energies than for x-rays of higher energy. Moreover, the x-ray optical trains disclosed in embodiments of the present invention typically have higher solid angle of collection for low energy x-rays than higher energy x-rays.

For most embodiments, it is preferred to achieve a combination of a large F and a small A in order to obtain low (better) absolute detection sensitivity.

X-Ray System.

FIG. 1 schematically illustrates one exemplary embodiment of the invention. The system comprises an x-ray source apparatus 80 that comprises an x-ray generator 08 that produces x-rays 888 with high brightness and a variety of x-ray energy spectra, an x-ray optical train 840 that collects a portion of x-rays 888 from the source and produces an x-ray beam 889 angularly collimated in the scattering plane (as shown) or a focused beam (not shown) to be incident on the sample 240 to be investigated at a grazing angle, and a variety of x-ray data collection systems, discussed further below.

The x-ray generator 08 comprises a vacuum environment (typically $10^{-6}$ torr or better) commonly maintained by a sealed vacuum chamber 20 or using active pumping, and manufactured with sealed electrical leads 21 and 22 that pass from the negative and positive terminals of a high voltage source 10 outside the vacuum chamber 20 to the various elements inside the vacuum chamber 20. The x-ray source 80 will typically comprise mounts 30 which secure elements of the x-ray generator 08 such as the vacuum chamber 20 to a housing 50, and the housing 50 may additionally comprise shielding material, such as lead, to prevent x-rays from being radiated by the source apparatus 80 in unwanted directions. Inside the vacuum chamber 20, an emitter 11 connected through the lead 21 to the negative terminal of a high voltage source 10, which serves as a cathode and generates a beam of electrons 111, often by running a current through a filament. Any number of prior art techniques for electron beam generation may be used for the embodiments of the invention disclosed herein.

A target 1100 comprising a target substrate 1000 and regions of x-ray generating material (shown in FIG. 1 as a set of embedded microstructures 700) is electrically connected to the opposite high voltage lead 22 and target support 32 to be at ground or positive voltage relative to the electron emitter 11, thus serving as an anode. The electrons 111 accelerate towards the target 1100 and collide with it at high energy, with the energy of the electrons determined by the magnitude of the accelerating voltage. The collision of the electrons 111 into the target 1100 induces several effects, including the emission of x-rays 888, some of which exit the vacuum chamber 20 and are transmitted through a window 40 that is transparent to x-rays.

The target 1100, as will be further described below, is configured to have multiple sub-sources of x-rays generated from points that are generally aligned with each other such that they produce x-rays that may have linear accumulation, leading to higher brightness. Microstructured targets such as those that may be used in embodiments of the invention disclosed herein have been described in detail in the co-pending US patent application entitled STRUCTURED TARGETS FOR X-RAY GENERATION (U.S. patent application Ser. No. 14/465,816, filed Aug. 21, 2014), which is hereby incorporated by reference in its entirety, along with the provisional applications to which it claims benefit. Furthermore, sources using these targets that have a linear accumulation of x-ray sources as are described more fully in the co-pending U.S. patent application entitled X-RAY SOURCES USING LINEAR ACCUMULATION by the inventors of the present invention (U.S. patent application Ser. No. 14/490,672 filed Sep. 19, 2014), which is also hereby incorporated by reference in its entirety, along with the provisional applications to which it claims benefit. Any of the target and source designs and configurations disclosed in the above referenced co-pending applications may be considered as alternative components and designs in any or all of the embodiments of the x-ray fluorescence systems according to the invention disclosed herein.

In some embodiments of the invention, there may also be an electron control mechanism 70 such as an electrostatic lens system or other system of electron optics that is controlled and coordinated with the electron dose and voltage provided by the emitter 11 by a controller 10-1 through a lead 27. The electron beam 111 may therefore be scanned, focused, de-focused, or otherwise directed onto a target 1100 comprising one or more microstructures 700 fabricated to be in close thermal contact with the substrate 1000. In addition to providing one or more electron beam(s) with predetermined properties (e.g. electron energy, current, and focal spot size), such a control mechanism 70 may also direct the respective electron beams to its desired position on one or more x-ray target(s) to generate x-rays at the positions of sub-sources along a predetermined direction.

The system will typically comprise an optical system to collect the x-rays from the source and direct them towards the sample 240 to be investigated. The combined x-ray source apparatus 80 and optical train 840 may be considered together to be an x-ray illuminator 800. The sample 240 is typically held in a mount 244, which may have motion controls for x-y- and z translation, as well as rotation about these axes as well.

The data collection system may comprise an x-ray detector or spectrometer 2900 and also an array x-ray detector 2900-R that collect fluorescence x-rays 2888 and reflected x-rays 2889, respectively, resulting from the interaction of the incident x-ray beam with the sample 240. Depending on the measurement technique being employed, the spectrometer 2900 may comprise x-ray optical elements and sensors designed to detect x-ray fluorescence and discriminate between x-ray energies while the array x-ray detector 2900-R may be designed to collect reflected x-rays, transmitted x-rays, diffracted x-rays, or scattered x-rays resulting from the interaction of the incident x-rays with the sample 240.

The spectrometer 2900 may comprise a photon counter, an energy dispersive detector such as a silicon drift detector or Si(Li) detector that can discriminate between the energies of the x-ray photons detected, a wavelength dispersive spectrometer, a micro-calorimeter, or an apparatus that comprises of a combination of one or more crystal or multilayer spectrometers and detectors to generate an electronic signal representing the number of counts for the fluorescent x-rays at various energies, or some other set of elements that converts x-ray intensity into an electronic signal. The array x-ray detector 2900-R may be any x-ray detector that converts x-ray intensity to an electronic signal, including linear detectors, position-sensitive array detectors, pin diodes, proportional counters, spectrometers, etc.

These electronic signals may be further processed by signal processing electronics 292 and passed to an analysis system 295 and presented to the user using a display 298. The sample 240 may be mounted in a holder 244. Such a sample holder 244 may be a simple tray, or comprise a complex mount, having controls 246 for translation of the sample in x, y and z directions, and may also include x, y, and/or z-axis rotation mechanisms, such as a goniometer.

Fluorescent x-rays tend to be emitted isotropically. For some applications, a spectrometer collecting emitted fluorescence x-rays over a larger collection angle will produce a better signal-to-noise ratio is preferred. In such a configuration the detector 290 shown is facing the sample 240 under examination. Note that this detector may be of any geometry (rectangular, square, hexagonal, honeycomb), and may also be a configuration with a through-hole, positioned such that the incident x-rays 887 actually pass through an aperture in the detector, such as the Rococo 2 (PNDetector GmbH; Munich, Germany).

Figure 2A:
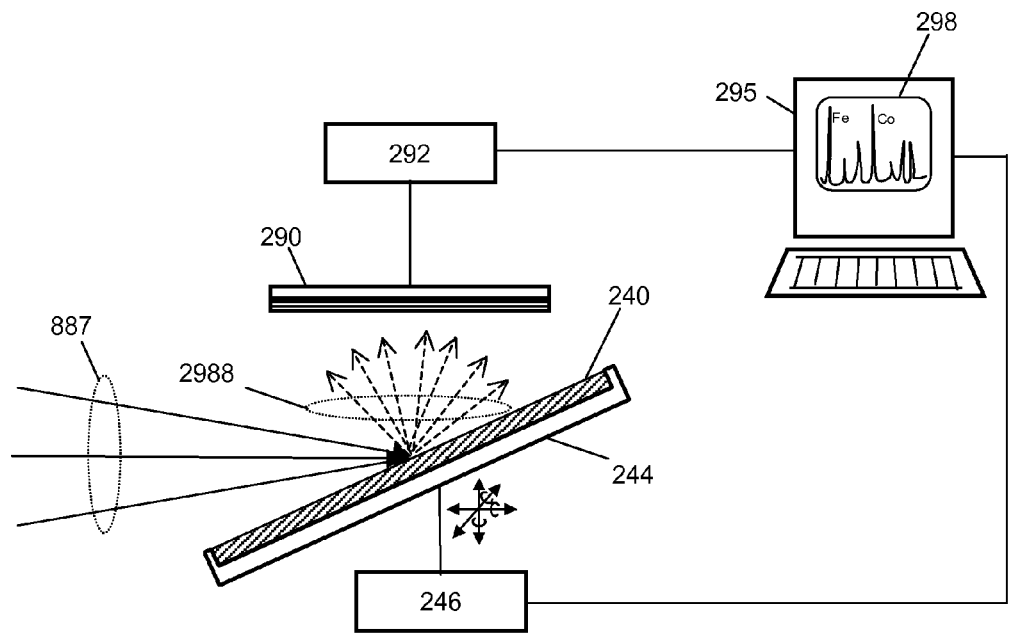
FIG. 2A schematically illustrates a converging beam x-ray fluorescence detection system for use in some embodiments of the invention.

If the working distance between the last optical element and the sample under investigation is too small to conveniently place a detector between them, a more conventional configuration such as that illustrated in FIG. 2A may be used in some embodiments of the invention. Here, instead of passing through an aperture in a detector, the incident x-rays 887 may pass through an aperture in a simple screen and converge on the sample 240 to be investigated. An x-ray fluorescence detector 290 with associated electronics 292 may be placed above the sample 240 to detect a portion of the emitted fluorescence, and pass the electronic signals to an analysis system 295 with a display 298.

Other detector geometries and arrangements for x-ray fluorescence may be known to those skilled in the art. For more on x-ray detectors, see Albert C. Thompson, "X-Ray Detectors", Section 4.5 of the X-ray Data Booklet [xdb.lbl.gov/Section4/Sec_4-5.pdf].

Figure 2B:
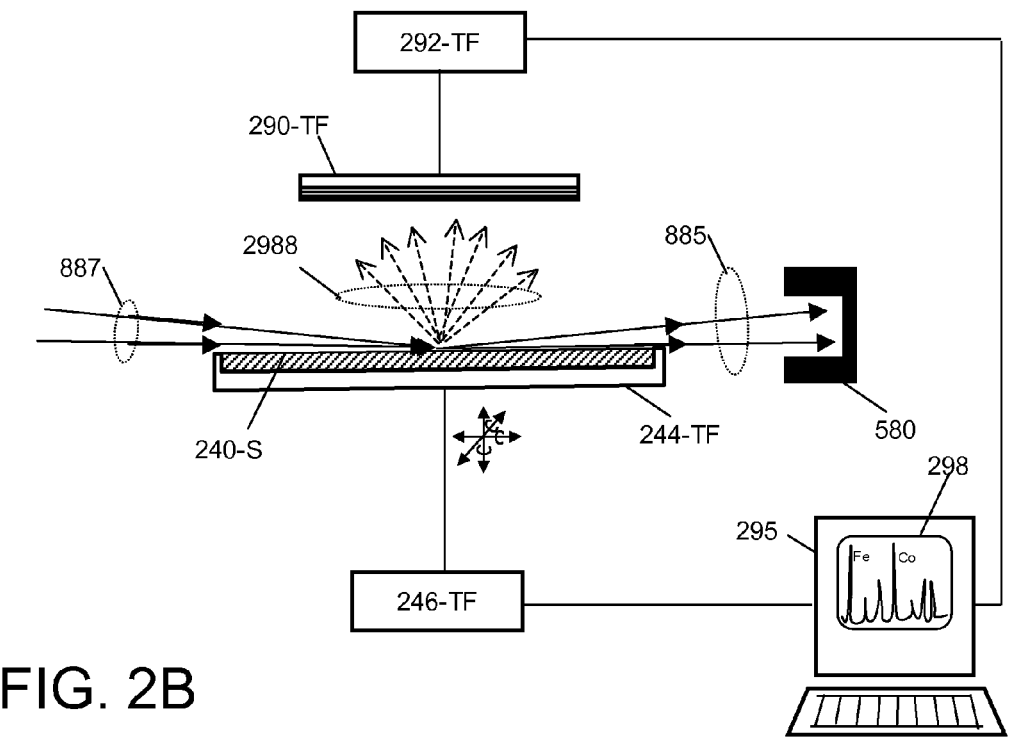
FIG. 2B schematically illustrates grazing incidence (total reflection) x-ray fluorescence detection system for use in some embodiments of the invention.

FIG. 2B illustrates an embodiment of the invention in which the analysis portion of the system is configured for total reflection fluorescence detection.

The system as illustrated comprises an x-ray optical system 800 comprising a source 80 comprising a target with microstructures 700 of x-ray generating materials bombarded by an electron beam 111, as well as optical elements 840 that focus the generated x-rays to a focused spot. A sample 240-S of material (typically a planar sample) to be examined is placed at or near that point of focus, supported by a sample holder 244-TF. This sample holder 244-TF may be a simple tray, or comprise a complex mount, having a controller 246-TF for translation of the sample in x, y and z directions, and may also include x, y, and/or z-axis rotation mechanisms, such as a goniometer.

Once the focused portion of the x-rays 887 converge onto the sample 240-S, x-ray fluorescence photons 2988 will propagate away from the sample 240. For TXRF, the detector apparatus (equivalent to the detector apparatus 2900 of FIG. 1) comprises a detector 290-TF arranged to capture x-ray fluorescence 2988 produced in predetermined directions, generally normal to the plane of the sample 240-S, while the reflected x-rays 885 will be absorbed using a beam stop 580. The detector 290-TF may be an electron drift detector that can discriminate between the energies of the x-ray photons detected, or may comprise a combination of a spectrometer and a detector, that generates an electronic signal representing the number of counts for the fluorescent x-rays at various energies, or some other set of elements that converts x-ray intensity into an electronic signal.

These electronic signals may be further processed by signal processing electronics 292 and passed to an analysis system 295 and presented to the user using a display 298.

The options for detectors for an embodiment comprising an analysis system used to measure TXRF signals will generally be the same as described above for the more general XRF case. Note: although the illustrations for FIGS. 2A-2D show the x-rays being focused onto the sample, other configurations using collimated beams may also be used in some embodiments of the invention.

Figure 2C:
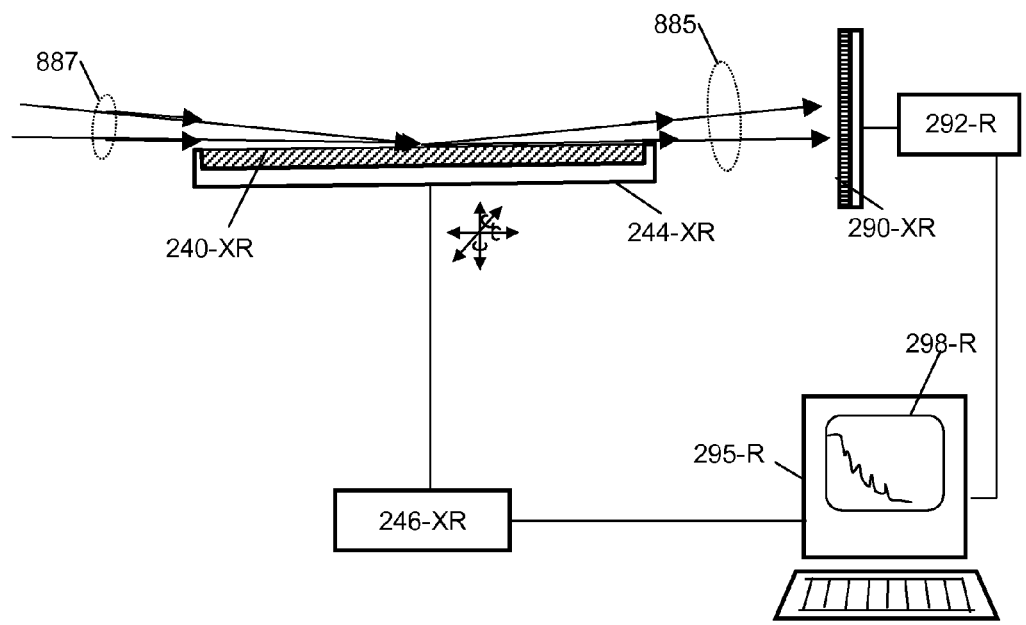
FIG. 2C schematically illustrates grazing incidence (total reflection) x-ray reflectance detection system for use in some embodiments of the invention.

FIG. 2C illustrates an embodiment of the invention in which the analysis portion of the system is configured for x-ray reflectometry detection.

The system as illustrated comprises an x-ray optical system 800 comprising a source 80 comprising a target with microstructures 700 of x-ray generating materials bombarded by an electron beam 111, as well as optical elements 840 that focus the generated x-rays to a focused spot. A sample 240-XR of material (typically a planar sample) to be examined is placed at or near that point of focus, supported by a sample holder 244-XR. This sample holder 244-XR may be a simple tray, or comprise a complex mount, having a controller 246-XR for translation of the sample in x, y and z directions, and may also include x, y, and/or z-axis rotation mechanisms, such as a goniometer.

Once the focused portion of the x-rays 887 converge onto the sample 240-XR, reflected x-ray photons 885 will propagate away from the sample 240-XR. For XRR, the detector apparatus (equivalent to the detector apparatus 2900-R of FIG. 1) comprises a detector 290-XR arranged to capture the reflected x-rays. The motion of the detector may be synchronized with the motion of the sample holder 244-XR to allow collection of reflectance data at a variety of angles, or may be fixed relative to the sample 240-S. The detector 290-XR may be an electron drift detector that can discriminate between the energies of the x-ray photons detected, or may comprise a combination of a spectrometer and a detector, that generates an electronic signal representing the number of counts for the fluorescent x-rays at various energies, or some other set of elements that converts x-ray intensity into an electronic signal.

These electronic signals may be further processed by signal processing electronics 292 and passed to an analysis system 295 and presented to the user using a display 298.

Figure 2D:
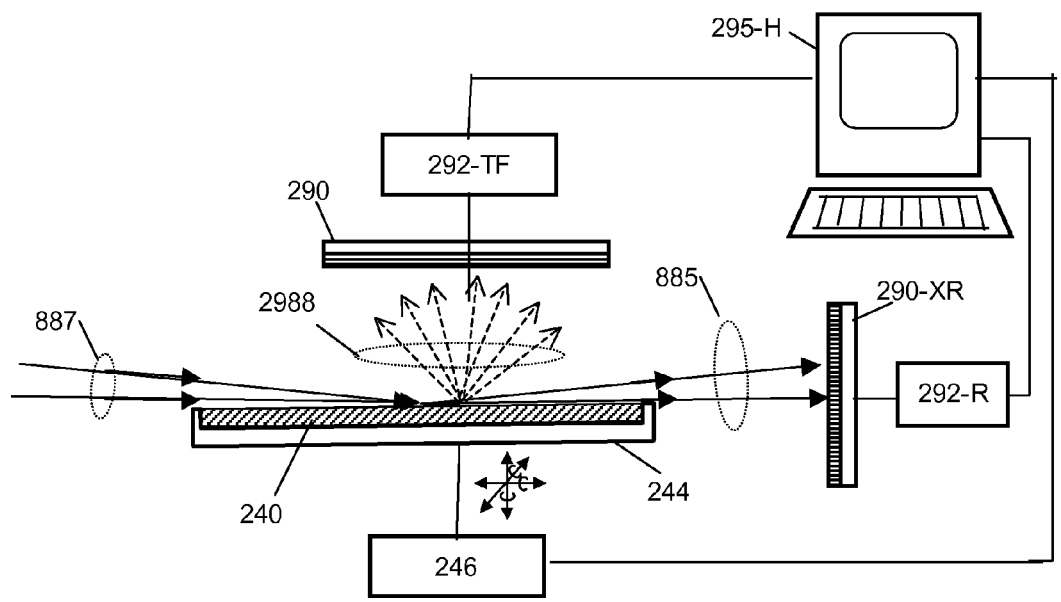
FIG. 2D schematically illustrates grazing incidence hybrid x-ray fluorescence and reflectance detection system for use in some embodiments of the invention.

In some embodiments, the analysis system 295 may also control the motions of the controller 246-XR to coordinate positions of the sample 240-S with the measured reflectometry results. In some embodiments, as illustrated in FIG. 2D, a hybrid system detecting both signals from a fluorescence detector 292-TF and a reflection detector 292-R may be displayed on a suitable hybrid analysis system 295-H.

X-Ray Source.

Figure 3:
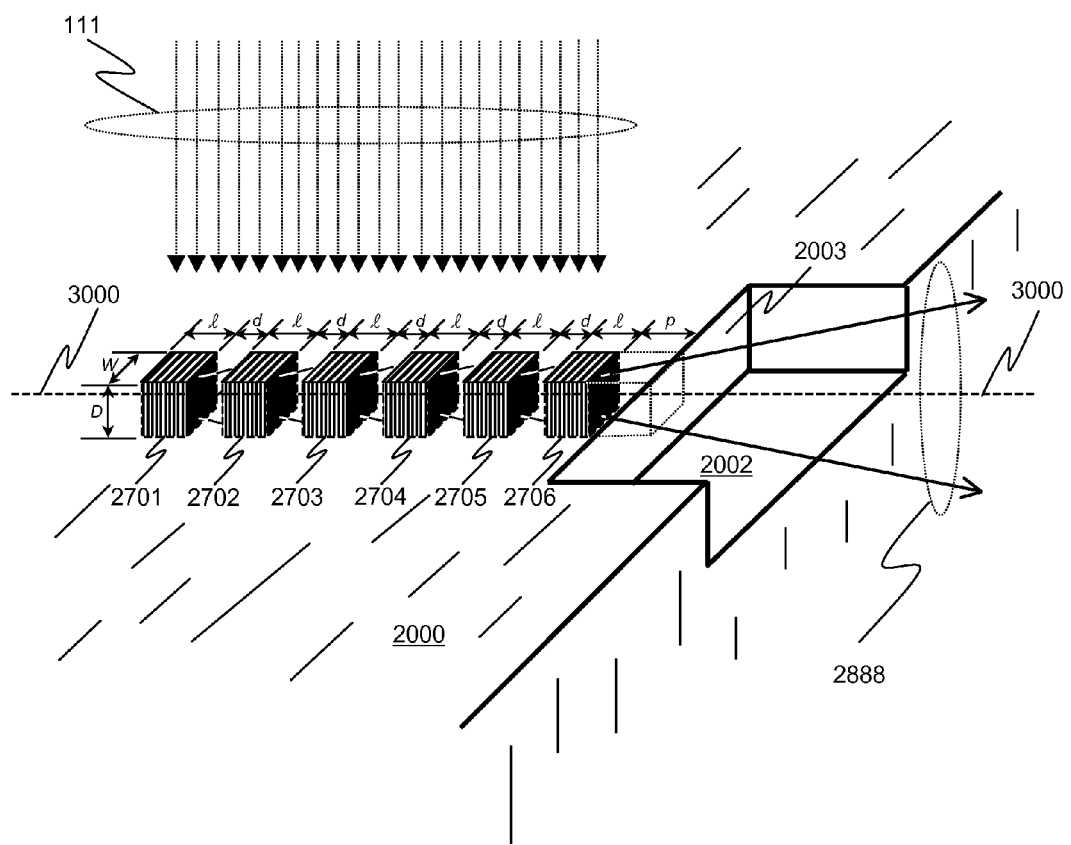
FIG. 3 schematically illustrates one embodiment of a linear accumulation x-ray source comprising sub-sources as used in some embodiments of the invention.

FIG. 3 schematically illustrates a portion of a linear accumulation x-ray source as may be used in some embodiments of the present invention that provides high x-ray brightness. In most embodiments, the linear accumulation x-ray source is preferred to have a focal spot of less than 1 micron to 300 microns. In this source, six discrete microstructures 2701, 2702, 2703, 2704, 2705, 2706 comprising x-ray generating materials selected for x-ray generating properties are embedded or buried in a substrate 2000 and configured at or near a recessed edge 2003 of the substrate 2000 by a shelf 2002, where the material of the substrate is of low average atomic number, high thermal conductivity and high melting point. The x-ray generating microstructures 2701, 2702, 2703, 2704, 2705, 2706 are arranged in a linear array along a predetermined axis 3000, and emit x-rays 2888 when bombarded with electrons 111. Along the direction within an angle $\psi$ of the axis 3000, x-rays generated in the six sub-sources accumulate and appear to be generated from a single sub-source. The angle range is approximately limited to smaller value of D and W divided by total length of the x-ray generating region 6*(1+d).

The thickness of the bar D (along the surface normal of the target) is selected to be between one-third and two-thirds of the depth of the incident electron penetrating into the substrate for optimal thermal performance, but it can be bigger or smaller. It may also be selected to obtain a desired x-ray source size in that direction which is approximately equal in combination with selecting sufficiently large acceleration energy of the incident electron beam as the penetration depth of the incident electron beam is approximately proportional to the energy of the electrons. The width of the bar W is selected to obtain a desired source size in the corresponding direction. Though W≈1.5 D is illustrated in FIG. 3, it could also be substantially smaller or larger, depending on the size of the source spot desired.

In FIG. 3, each of the discrete microstructures 2701, 2702, 2703, 2704, 2705, 2706 shown to have equal a length l along the axis 3000. The total length of all the six discrete microstructures 6 l will commonly be set to be ~2 L, where L is the x-ray linear attenuation length of the materials of the discrete microstructures for the x-ray energy of interest, but a value of 0.5 L to 4 L may be selected. The thickness of the substrate material between two adjacent discrete microstructures is may a value between 0.5 l to 3 l, optimized by considering the relative thermal conductivity and mass density of the materials of the substrate and the discrete microstructures, and the x-ray linear attenuation length of the substrate at the x-ray energy of interest, and the desired convergence angle ψ.

The selection of the materials of the linear accumulation source target used in some embodiments is such that the substrate (the first material) is of low Z material with high thermal conductivity, such as diamond or beryllium, and the material of the sub-sources (the second material) are selected for x-ray generating properties such as spectral characteristics and x-ray production efficiency and may include (but are not limited to) copper, molybdenum, and tungsten. In some embodiments, the thermal conductivity of the targets is mainly determined by the thermal conductivity of the substrate material, which allows the use of x-ray generating materials with lower thermal conductivity otherwise not suitable as x-ray target materials in a contiguous single material target employed in prior art, such as germanium and lead, consequently allow more choice of elements to produce characteristic x-ray lines.

In one embodiment of the linear accumulation x-ray source of the present invention, the incident electron beam uniformly illuminates the area of the substrate containing the discrete microstructures (as shown in FIG. 3). Because electron energy deposition rate in a material is proportional to the mass density, the ratio of the energy deposited in the substrate between two adjacent discrete microstructures and the discrete microstructures is approximately equal to the ratio of the their mass relative mass density. In some embodiments of the invention, the incident electron beam is spatially modulated so that a large fraction of the electron beam is incident on the discrete microstructures. This makes efficient use of the incident electron energy for x-ray production and reduces the electron energy deposition in the substrate and improves thermal dissipation of the discrete microstructures.

Because each of the discrete microstructures has five faces transferring heat into the substrate, increasing the heat transfer away from the discrete microstructures 2701-2706 and into the substrate. As illustrated, the separation between the sub-bars is a distance d≈1, although larger or smaller dimensions may also be used, as discussed above.

The distance between the edge of the shelf and the edge of the x-ray generating material p as illustrated is p≈W, but may be selected to be any value, from flush with the edge 2003 (p=0) to as much as 5 mm, depending on the x-ray reabsorption properties of the substrate material for the x-ray energy of interest, the relative thermal properties of the materials of the substrate and the discrete microstructures, and the amount of heat expected to be generated when bombarded with electrons. For example, in some embodiments it may be generally preferred that the x-ray transmission through the edge of the shelf and the edge of the x-ray generating material p as illustrated is greater than 50%. X-rays that are generated are collected from the side of the anode, most preferably at near-zero take-off angles.

Figure 4:
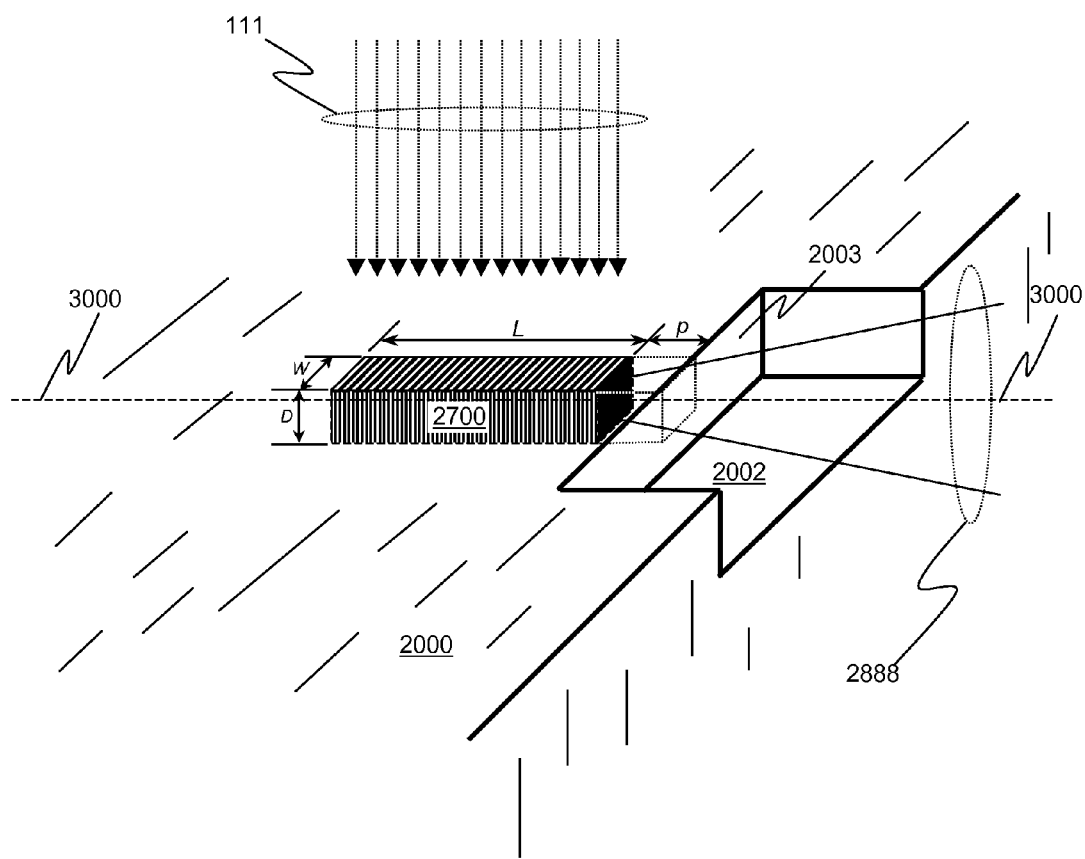
FIG. 4 schematically illustrates one embodiment of a linear accumulation x-ray source comprising a monolithic x-ray source as used in some embodiments of the invention.

Although the microstructures shown in FIG. 3 are of rectangular prisms of equal size, other any number of shapes and sizes can be used to achieve high x-ray source brightness using the linear accumulation design principle from plural of sub-sources and the use of the discrete microstructures embedded or buried in a substrate to improve the thermal dissipation property of the x-ray generating material of each sub-source, such as cubes, rectangular blocks, regular prisms, right rectangular prisms, trapezoidal prisms, spheres, ovoids, barrel shaped objects, cylinders, triangular prisms, pyramids, tetrahedra, or other particularly designed shapes, including those with surface textures or structures that enhance surface area, to best generate x-rays of high brightness and that also efficiently disperse heat. Furthermore, the x-ray generating material in each of the sub-sources may not be of single uniform material but comprise additional finer structures of x-ray generating material. FIG. 4 schematically illustrates a portion of an embodiment of the present invention comprising a single microstructure 2700 instead of the discrete microstructures of FIG. 3. In this illustration, the width W and depth D into the substrate of the microstructure 2700 are the same as in FIG. 3, while the accumulated length L of the microstructure 2700 is equal to 6 l. In other words, the volume of the x-ray generating material in FIGS. 3 and 4 are the same, and similar volume of x-rays may be produced by similar excitation by an electron beam 111. Similar design considerations on D, W, L, and p for FIG. 3 apply here.

Figure 5:
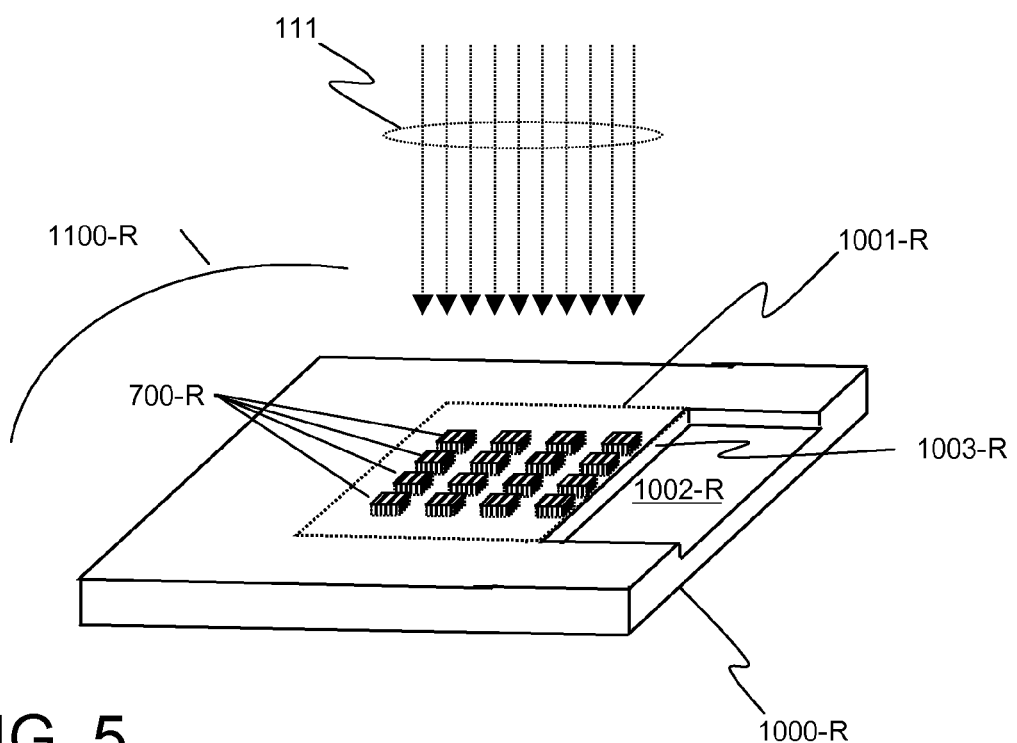
FIG. 5 schematically illustrates a linear accumulation x-ray source as used in some embodiments of the invention in which multiple sub-sources are embedded in a substrate with a recessed shelf.

In FIG. 5, a variation of the source target used in some embodiments is shown in which a two-dimensional array of microstructures is embedded in a substrate, and works in a similar principle to the one-dimensional array of microstructures described in FIG. 3. Each of the microstructures 700-R acts as a sub-source of x-rays when bombarded by an electron beam 111. The combination of the high thermal conductivity of the substrate and the small dimension of the discrete microstructures allows heat to be efficiently drawn out of the x-ray generating material, in turn allows bombardment of the discrete microstructures with higher electron density and/or higher energy electrons, which leads to greater x-ray brightness and flux.

It should also be noted here that, when the word "discrete microstructure" is used herein, it is specifically referring to microstructures comprising x-ray generating material. Likewise, it should be noted that, although the word "discrete microstructure" is used, x-ray generating structures with dimensions smaller than 1 micron, or even as small as nano-scale dimensions (i.e. greater than 10 nm) may also be described by the word "discrete microstructures" as used herein as long as the properties are consistent with the geometric factors for sub-source size and pitches set forth in the various embodiments.

It should also be noted that here that, when the word "sub-source" is used it may refer to a single discrete microstructure of x-ray generating material, or an ensemble of smaller microstructures of x-ray generating materials, illuminated by a single electron beam.

The x-ray generating material used in the target should have good thermal properties, such as a high melting point and high thermal conductivity, in order to allow higher electron power loading on the source to increase x-ray production. The x-ray generating material should additionally be selected for good x-ray production properties, which includes x-ray production efficiency (proportional to its atomic number) and in some cases, it may be desirable to produce a specific spectra of interest, such as a characteristic x-ray spectral line. For example, targets are often fabricated using tungsten, with an atomic number Z=74, due to its efficient x-ray production and its high thermal conductivity.

Additionally, in FIG. 5, the target 1100-R comprises a substrate 1000-R with a recessed shelf 1002-R. This allows the region 1001-R comprising an array of microstructures 700-R to be positioned flush with, or close to, a recessed edge 1003-R of the substrate, and emit x-rays at or near zero angle without being reabsorbed by the substrate 1000-R, yet provides a more symmetric heat sink for the heat generated when exposed to electrons 111. The two-dimensional array enables a line source when viewed at a zero degree take-off angle.

Figure 6:
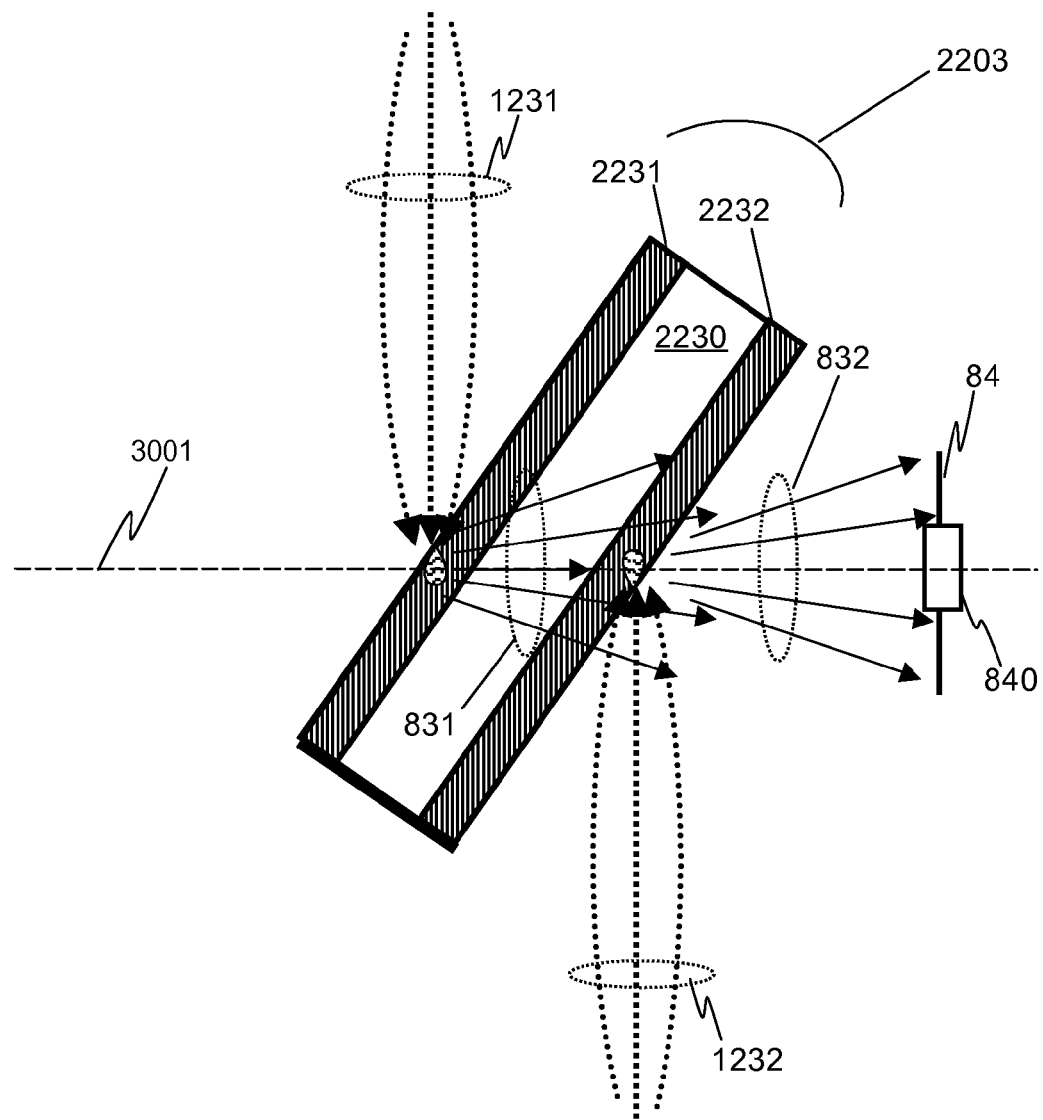
FIG. 6 schematically illustrates a cross section of a two-sided linear accumulation x-ray source as used in some embodiments of the invention FIG. 7 schematically illustrates a cross section of a two-sided linear accumulation x-ray source having an anode comprising discrete microstructures embedded or buried in a substrate as used in some embodiments of the invention.

FIG. 6 schematically illustrates an embodiment of the linear accumulation x-ray source employed in various x-ray source embodiments of the present invention that comprises two sub-sources with targets sharing a common substrate 2230. The substrate may be a first material of low atomic number, low mass density, high thermal conductivity and high melting point, aligned to increase linear accumulation of x-rays along an axis 3001 connecting the two sub-sources. In this embodiment, the source will have two electron beams 1231 and 1232 that are controlled to bombard the respective x-ray generating materials 2231 and 2232 coated on the common substrate 2230 and generate x-rays 831 and 832, respectively.

The x-ray generating materials are sufficiently thick for efficient generation of x-rays of desired spectra but sufficiently thin for high transmission of the desired x-rays. The underlying principle is that the electron penetration depth is typically much smaller than the x-ray linear attenuation length, especially for higher energy x-rays. The thickness of the x-ray generating materials 2231 and 2232 is typically selected to be less than or comparable to the depth of the incident electron beam penetrating into the x-ray generating materials 2231 and 2232, a larger value may be used. If the bombardment occurs at an angle to the surface normal, as illustrated, the angle of incidence can also affect the selection of the coating thickness. Although the tilt of the targets 2203 and 2204 relative to the electron beams 1231, 1232 and 1222 is shown as ~45°, any angle from 0° to 90° that allows x-rays to be generated may be used.

The material of the common substrate 2230 is typically selected from a material of low Z material with high thermal conductivity, such as diamond, diamond like material, and beryllium, and silicon carbide. The thickness of the common substrate is selected to have high x-ray transmission for the x-ray energy of interest, often greater than 50%. The distance between the two sub-sources is generally greater than the incident electron beam size.

It is possible that one or more of the anodes of the sub-sources has a very thin substrate or even zero thickness in the impact region of the electron beam(s). It is typical that the anodes (with or without the substrate) of the sub-sources are supported on a support frame with an opening reasonably larger than the incident electron beam or x-ray source size. The support frame will typically have high thermal conductivity and may be cooled using techniques well known to those skilled in the art. In some embodiments, the frame will be cooled to a temperature of minus 90 centigrade when the substrate or the frame is made of diamond to make use of the increased thermal conductivity of diamond with decreasing temperature.

Figure 7:
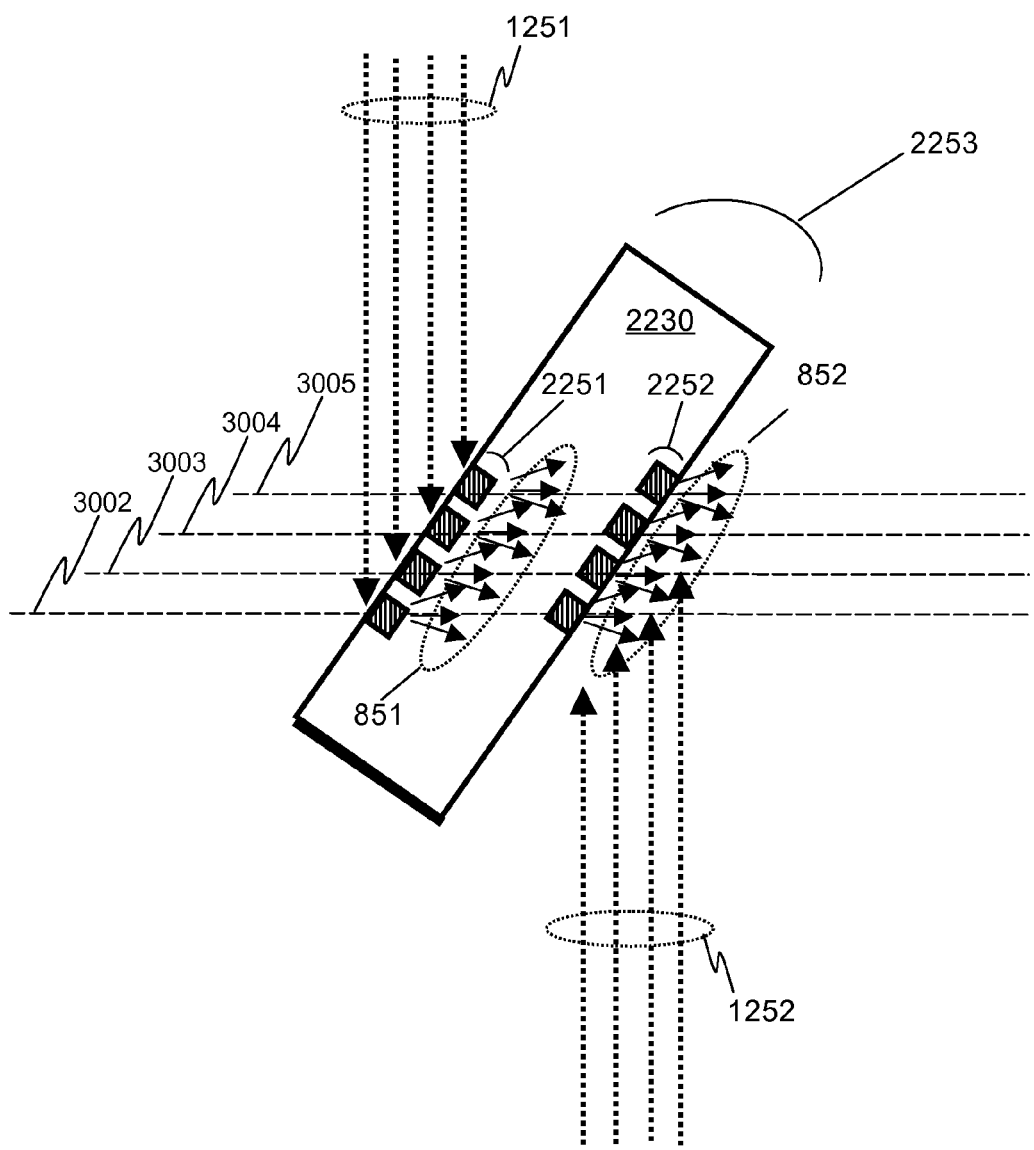

Though the x-ray sub-sources 2231 and 2232 in FIG. 6 are shown as extended targets comprising a layer of single material, in other embodiments at least one of the single material layer target may be replaced with a region comprising a plurality of discrete microstructures of x-ray generating materials embedded or buried in the common substrate 2230, such as those illustrated in FIG. 7. In this figure, each of the discrete microstructures in the sets of microstructures 2151 and 2152 acts a sub-source x-ray source when illuminated by an electron beam. When aligned with each other along axes 3002-3005, these also produce a higher brightness x-ray beam with an extended beam profile that operates on the same principle the source as illustrated in FIG. 6.

Figure 8:
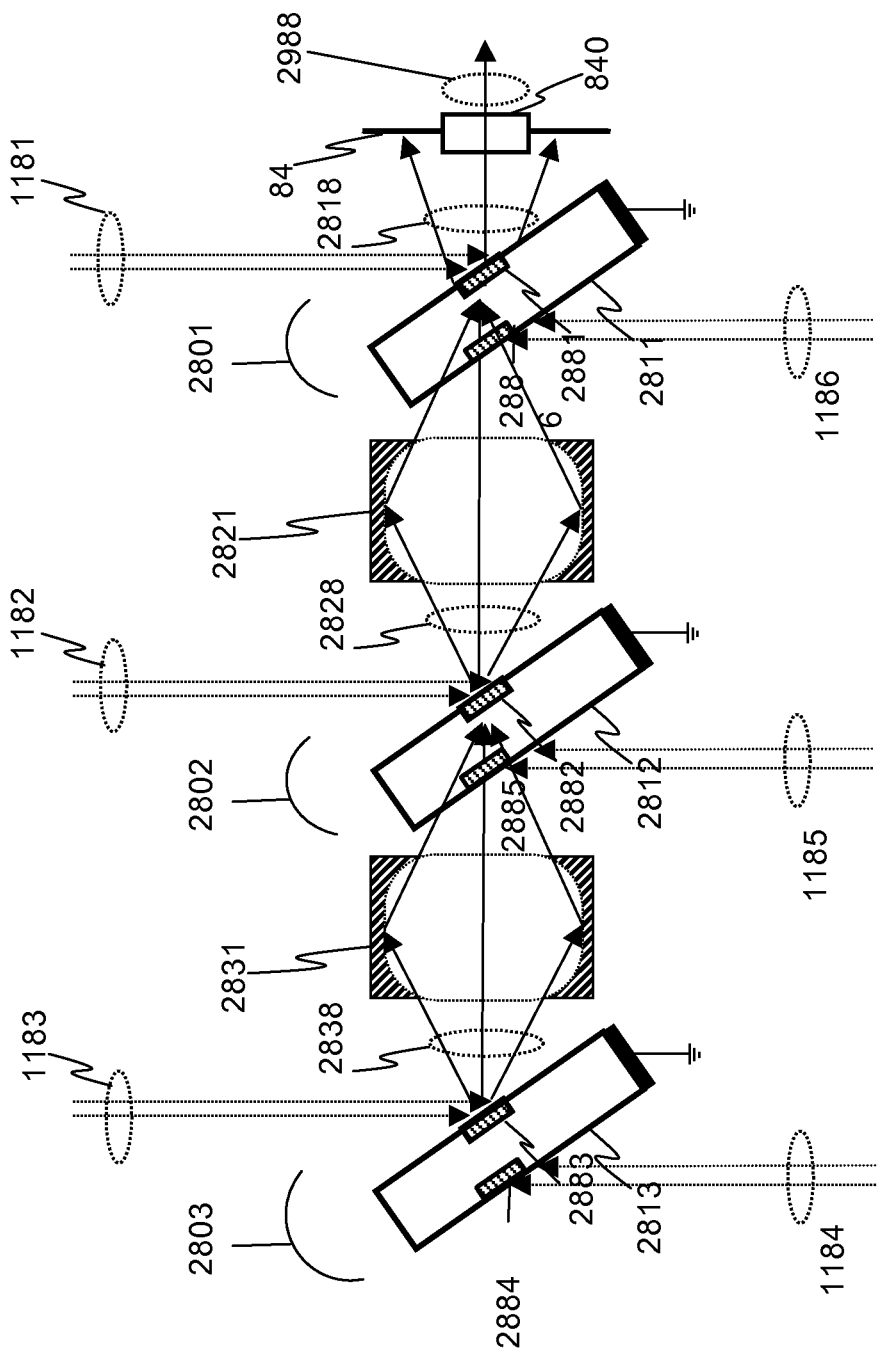
FIG. 8 schematically illustrates a linear accumulation x-ray source comprising optics between sub-sources as used in some embodiments of the invention

FIG. 8 schematically illustrates yet another embodiment of the linear accumulation x-ray source employed in various embodiments of the present invention that comprises a plurality of sub-sources 2801, 2802, and 2803 with x-ray targets fabricated on at least two separate substrates, aligned along a predetermined axis. At least one x-ray imaging optic (2821 or 2831) that collects and image x-rays from one sub-source, for example, 2886, to another sub-source on, for example, 2885, on a different substrate so that x-rays from the two sub-sources appear to originate from a single sub-source viewed along the axis, achieving linear accumulation of x-rays from the two sub-sources to achieve high brightness. Each of the sub-sources comprises a corresponding electron beam (1181, 1182, 1183, 1184, 1185, and 1186) and an x-ray target containing an x-ray generating material. The x-ray target may be a layer of the x-ray generating material deposited on its respective substrate, as illustrated, or comprise plural of the discrete microstructures fabricated in close thermal contact with (such as embedded in or buried in) with its respective substrate, as was illustrated in FIG. 7.

To preserve the brightness of the sub-sources, the x-ray imaging optic that collects the generated x-rays is may have a point spread function less than the effective source size of the two sub-sources, the smaller one if two sub-sources have different source sizes. The focusing efficiency of the x-ray imaging optic 2831 and/or 2832 is may be designed to be greater than 50%. Variations of the optics 2831 and/or 2832 may include focusing optics illustrated in FIGS. 11, 12, and 13. Characteristics of the substrate may be similar to those described in FIG. 6.

The anode targets shown in FIGS. 1 through 8 may be cooled using methods known in the art, such as water cooling, thermoelectric cooling, and/or heat pipes, which may also be employed to increase the thermal performance of the anode and thus the brightness of the x-ray source.

A second objective of the invention is to enable x-ray sources that produce sufficiently bright characteristic x-rays of desired spectra from element(s) whose materials are of poor thermal property, including low thermal conductivity, low melting point, or both. In one example, the element is titanium (Ti) and the material is a Ti metal or a Ti compound, whose Kα x-rays have significantly larger fluorescence cross sections for many biologically important elements including phosphorus, sulfur, chlorine, selenium, and low Z elements like oxygen, nitrogen, and fluorine, than those at 8 keV or higher energy x-rays. Despite the need for characteristic x-rays of several of these elements in TXRF applications (to increase fluorescence of particular element(s), or to suppress background signal from x-ray scattering and fluorescence from the other element(s) within the sample or material of the substrate), many elements like Ti have largely excluded them from use in conventional x-ray sources because of inferior thermal property. The structured anode design overcomes this limitation.

Any number of prior art techniques for generating electron beam may be used for the embodiments of the linear accumulation x-ray source disclosed herein. Additional known techniques used for electron beam generation include heating for thermionic emission, Schottky emission (a combination of heating and field emission), emitters comprising nanostructures such as carbon nanotubes), and by use of ferroelectric materials. [For more on electron emission options for electron beam generation, see Shigehiko Yamamoto, "Fundamental physics of vacuum electron sources", Reports on Progress in Physics vol. 69, pp. 181-232 (2006)]. It is preferred that the size of the electron beam is optimized according to the x-ray source size desired.

Some embodiments use x-ray generating material (the second material) comprised of predetermined characteristic spectral lines to enable optimal fluorescent x-ray generation for a group of elements of interest or to suppress characteristic fluorescence x-rays from a major matrix element in the sample to reduce signal background in TXRF, or optimize scattering cross in GISAXS, or optimize refractive index contrast between layers in XRR.

In some embodiments of the invention, there may also be one or more electron optical systems that, in addition to providing electron beam(s) with predetermined property (electron energy, current, and focal spot size), can control and direct the respective electron beams to its desired position on the respective x-ray target to incident on the respective x-ray generating material and/or align the sub-sources along a predetermined direction.

X-Ray Optical Train.

Various embodiments of the x-ray surface analysis and measurement apparatus comprise an x-ray optical train to collect a portion of x-rays from the linear accumulation x-ray source, subsequently spectrally filter, collimate or focus the x-rays to produce an x-ray beam to be incident on the sample to be analyzed, depending on the desired performance of the x-ray surface analysis and measurement system in terms of desired measurement parameters, such as spatial resolution, throughput, and element analysis sensitivity and accuracy. It should be noted that in the variations of optical trains illustrated as cross-sections in the following figures that the optics may be axially symmetric and also have either an absorbing beam stop, slit, or aperture that absorbs X-rays that are not reflected.

Optical trains such as those that may be used in embodiments of the invention disclosed herein have been described in detail in the co-pending US patent application entitled X-RAY ILLUMINATORS WITH HIGH FLUX AND HIGH FLUX DENSITY (U.S. patent application Ser. No. 14/544,191, filed Dec. 5, 2014), which is hereby incorporated by reference in its entirety, along with the provisional applications to which it claims benefit.

To improve the numerical aperture of the optical elements of the optical train, some embodiments of the invention may use coatings on the reflective surface. These coatings are preferably high density materials (greater than 2.5 g/cm$^3$) such as platinum, iridium, or gold and are typically around a few angstroms to a few nanometers in thickness. Such high density coatings provide a larger critical angle for reflection, enabling the collection of more x-rays. Alternatively, multilayer coatings that reflect x-rays using alternating periodic layers of two or more materials provide constructive interference in reflection for certain wavelengths. The reflection efficiency depends on the wavelength and angle of incidence of the x-rays, as well as the thickness of the alternating layers, so this has limited use as a broadband reflector, but may be used if specific wavelengths are desired. Combinations that may be used for multilayer reflectors may be tungsten/carbon (W/C), tungsten/tungsten silicide (W/WSi$_2$), molybdenum/silicon (Mo/Si), nickel/carbon (Ni/C), chromium/scandium (Cr/Sc), and lanthanum/boron carbide (La/B$_4$C), and tantalum/silicon (Ta/Si), among others. The surface may also be a compound coating comprising an alloy or mixture of several materials.

In some embodiments, the optics may furthermore be nested (concentric within each other) to allow greater collection of x-rays, as is typical with the non-axial symmetric mirrors used commonly in x-ray astronomy.

Figure 9:
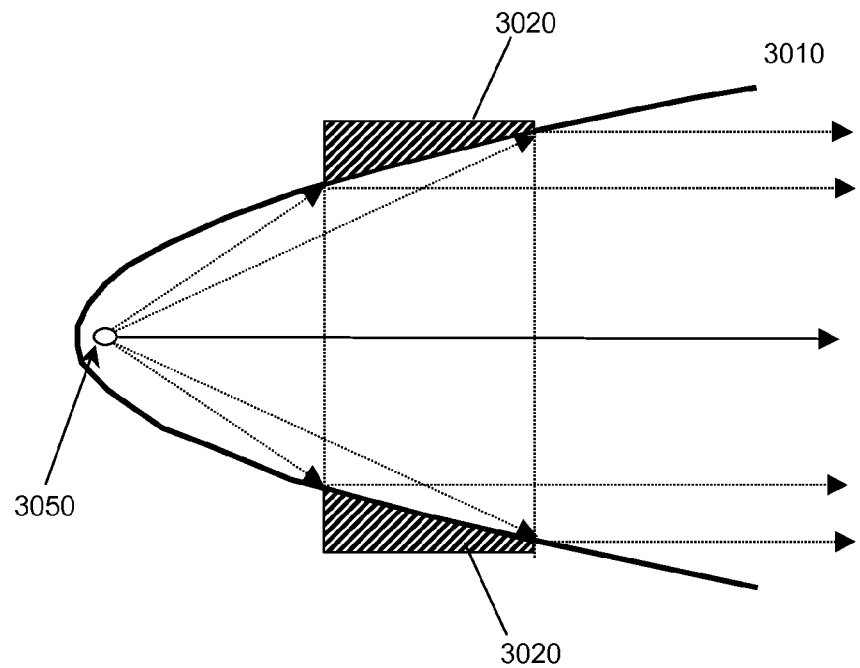
FIG. 9 illustrates a cross section of a paraboloidal optical element.
Figure 10:
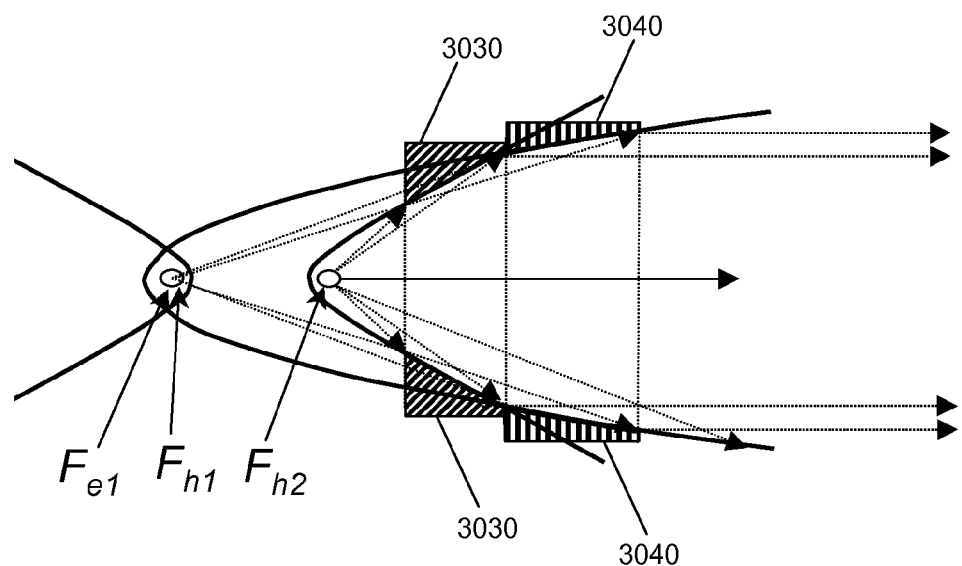
FIG. 10 illustrates a cross section of a Wolter Type I optical element.

FIGS. 9 and 10 schematically illustrate variations of optical train components to produce a collimated high brightness x-ray beam. FIG. 9 illustrates a cross-section of an x-ray mirror 3020 of which the interior reflecting surface is of portion of a paraboloid 3010. It is configured that its focus 3050 will be positioned with the center of the linear accumulation x-ray source and its axis is aligned along the axis of the linear accumulation x-ray source, such as was illustrated by the axis 3000 in FIG. 3. The x-ray mirror 3020 collects x-rays from the source and generates a collimated x-ray beam. As the source will not be a perfect point source, the angular convergence of the collimated beam is approximately equal to the apparent linear accumulation x-ray source divided by the distance between the source and the entrance of the x-ray mirror 3020. In some embodiments, the angular convergence of the collimated beam in the scattering plane to be smaller than the critical angle for total reflection of the sample. Otherwise, additional slit(s) may be used in the optical train to obtain the desired angular collimation in the scattering plane.

The surface profile of the x-ray mirror may be designed such that the x-rays with the desired x-ray energy incident on the x-ray mirror surface at a grazing angle smaller than or equal to the critical angle for total reflection of the mirror surface material at the desired x-ray energy. The mirror surface material may be glass, or coated either with a high mass density material to increase the critical angle for total reflection to collect more x-rays from the linear accumulation x-ray source. The mirror surface may also be coated with a multilayer of appropriate material composition, d-spacing gradient, and appropriate d-spacing gradient along the optical axis, to increase solid angle of x-ray collection from the linear accumulation x-ray source and obtain an x-ray beam with narrow spectra.

FIG. 10 schematically illustrates a cross-section of another optical train that may be used in embodiments of the presentation invention to produce a collimated high brightness x-ray beam. The optical train in this example comprises a type I Wolter mirror optic having an ellipsoid and a hyperboloid, both aligned so one of the foci of the ellipse $F_{el}$ corresponds to one of the foci of the hyperbola $F_{hl}$.

The type I Wolter mirror is typically configured such that the focus $F_{hl}$ will be positioned at the center of the linear accumulation x-ray source and its optical axis is aligned to correspond to the axis of the linear accumulation x-ray source, such as was illustrated by the axis 3000 in FIG. 3. Similar to the parabolic optic of FIG. 9, it is preferred that the angular convergence of the collimated beam in the scattering plane is smaller than the critical angle of the sample.

The slopes and surface profiles of the x-ray optics are designed such that the x-rays with the desired x-ray energy are incident on the x-ray mirror surface at a grazing angles that are smaller than or equal to the critical angle of the mirror surface material for total at the desired x-ray energy. The surface material of one or both mirror components may be glass, or coated either with a high mass density material to increase the critical angle for total reflection, which is proportional to the square root of the density of the material. The mirror surface may also be coated with a multilayer of appropriate material composition, d-spacing gradient, and appropriate d-spacing gradient along the optical axis, to increase solid angle of x-ray collection from the linear accumulation x-ray source and obtain an x-ray beam with narrow spectra. Compared with the single paraboloid mirror illustrated in FIG. 9, the type I Wolter mirror illustrated in FIG. 10 can have up to 4× the solid angle of collection of x-rays from the linear accumulation x-ray source, resulting in a collimated x-ray beam with a larger x-ray flux.

The x-ray optical train illustrated in FIGS. 9 and 10 may further comprises a spectral filtering component to narrow the energy spectra of the collimated x-ray known in the prior art, such as a thin foil spectral filter, or multilayer or crystal monochromator. Additionally, it may also compromise aperture(s) or slit(s) to obtain a desired beam shape and size, as will be known by those skilled in the art.

Figure 11:
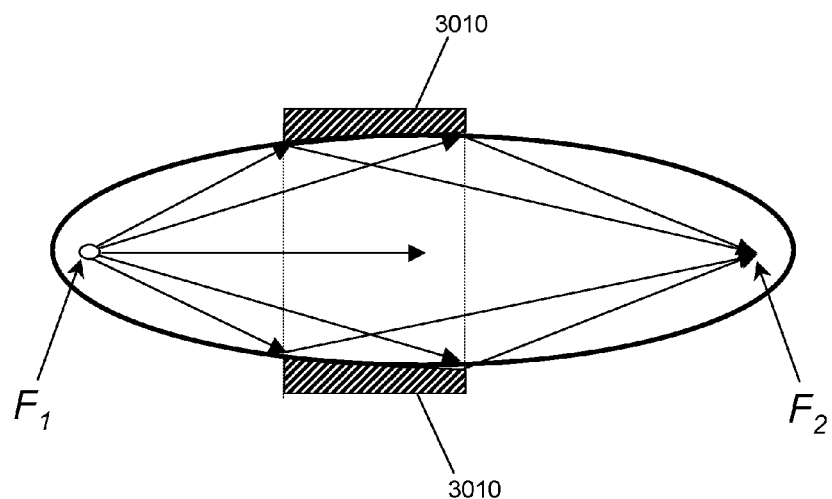
FIG. 11 illustrates a cross section of an ellipsoidal optical element.
Figure 12:
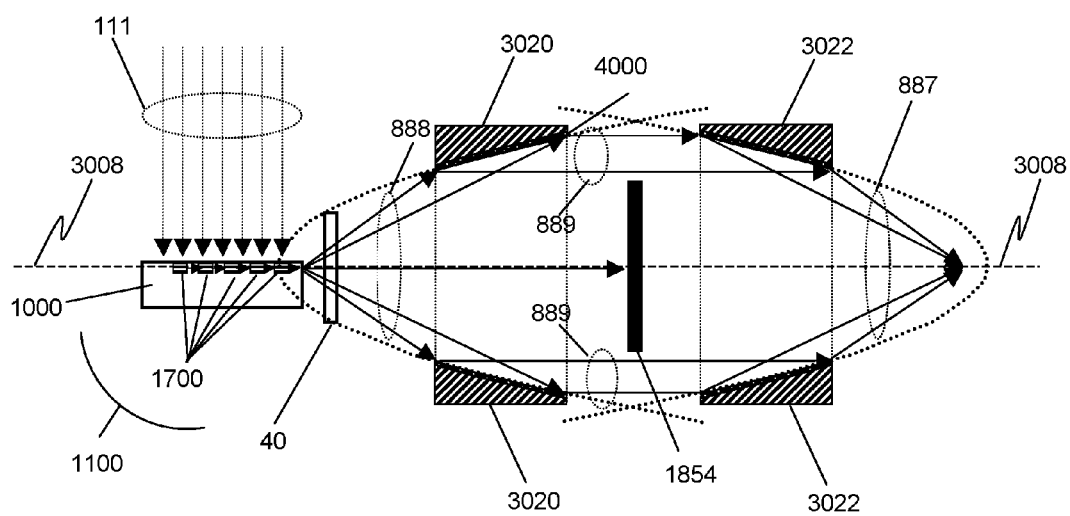
FIG. 12 illustrates a cross section of an x-ray source with linear accumulation and two symmetric parabolic optics as used in some embodiments of the invention.
Figure 13:
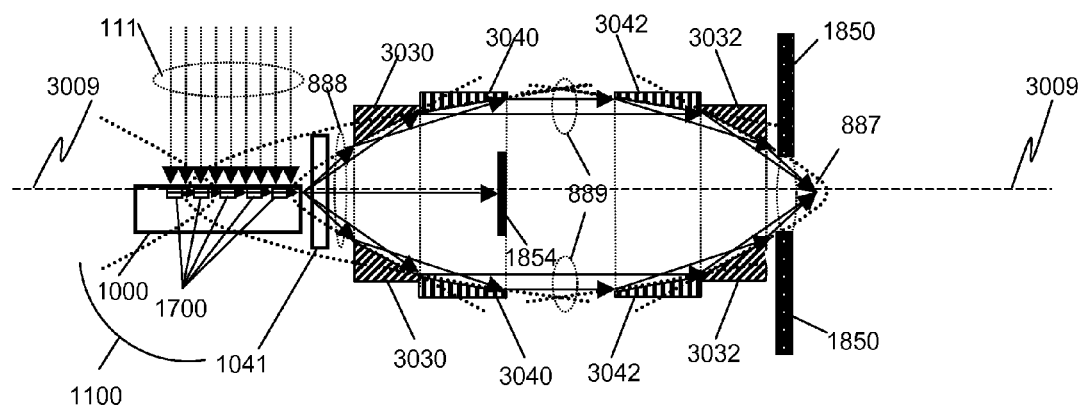
FIG. 13 illustrates a cross section of an x-ray source with linear accumulation two symmetric Wolter type I optics as used in some embodiments of the invention.

In addition to collimating optics, variations of optics for the optical train of embodiments may use focusing optics such as are shown in FIGS. 11, 12, and 13. It should be noted that like the collimating optics, all optical mirror surface materials may be glass, or coated either with a high mass density material. The mirror surface may also be coated with a multilayer of appropriate material composition, d-spacing gradient, and appropriate d-spacing gradient along the optical axis, to increase solid angle of x-ray collection from the linear accumulation x-ray source and obtain an x-ray beam with narrow spectra.

FIG. 11 schematically illustrates an embodiment of the presentation invention to produce a high brightness focused x-ray beam for increasing x-ray flux density on the sample, or for small spot analysis or measurement spatially resolved mapping with TXRF, DIXRD, and GISAXS, or for increasing x-ray flux density. The optical train comprises an x-ray mirror 3010 of which the reflecting surface corresponds to a portion of an ellipsoid. It is configured that one of its foci F, is positioned with the center of the linear accumulation x-ray source and its axis is aligned to the axis of the linear accumulation x-ray source, such as was illustrated by the axis 3000 in FIG. 3). This configuration generates a bright, focused x-ray beam. The surface profiles of the x-ray mirrors are designed such that the x-rays with the desired x-ray energy incident on the x-ray mirror surface at a grazing angle smaller than or equal to the critical angle for total reflection of the mirror surface material at the desired x-ray energy.

FIG. 12 schematically illustrates another focusing optic that may be used in the optical train of some embodiments of the invention comprising a first x-ray mirror 3020 of which the reflecting surface corresponds to a portion of a paraboloid. It is configured so that its focus is positioned with the closest edge of the last of the sub-sources 1700 in the linear accumulation x-ray source 1100 and its axis is aligned to the axis 3008 of the linear accumulation x-ray source 1100. The x-ray mirror 3020 collects x-rays from the source 1100 and generates a collimated x-ray beam 889. A central beam stop 1854 that blocks non-reflected x-rays passing through the center of the x-ray optic 3020 is also shown. A second x-ray mirror 3022, of which the reflecting surface corresponds to a portion of a paraboloid, is aligned with the first x-ray mirror 3020 so that they are symmetric with their axes are aligned, such that the collimated x-rays 889 are focused to produce a focused x-ray beam 887. The surface profiles of the x-ray mirrors are designed such that the x-rays with the desired x-ray energy incident on the x-ray mirror surface at a grazing angle smaller than or equal to the critical angle for total reflection of the mirror surface material at the desired x-ray energy. Compared with the single ellipsoid x-ray mirror illustrated in FIG. 11, the current configuration provides more x-rays collected from the linear accumulation x-ray source, resulting in a focused x-ray beam with a larger x-ray flux.

Although FIG. 12 shows a second paraboloidal optical element 3022 of the same size and shape as the initial paraboloidal optical element 3020, these need not be the same dimensions, but may have paraboloid surfaces with different geometric parameters. By selecting appropriate parameters, the x-ray optical train can be designed to demagnify the x-ray source to produce a small focused x-ray beam on to the sample or magnify the x-ray source to produce a large focused beam on to the sample.

It should be noted that, although only certain embodiments of a linear accumulation x-ray source have been illustrated, other embodiments of linear accumulation x-ray sources can be used as well.

FIG. 13 schematically illustrates another embodiment of the presentation invention to produce a high brightness focused x-ray beam. The x-ray optical train comprises two type I Wolter mirrors: the first one comprising an ellipsoidal mirror 3030 and a hyperboloidal mirror 3040, is configured such that its focus is positioned at the center of the linear accumulation x-ray source and its optical axis is aligned the axis 3009 of the linear accumulation x-ray source 1100; and the second one comprising a hyperboloidal mirror 3042 and an ellipsoidal mirror 3032, is aligned such that its optical axis is aligned with that of the first Wolter mirror to receive x-rays reflected by the first Wolter mirror and produce a bright, focused x-ray beam. This configuration allows more x-rays to be collected from the linear accumulation x-ray source, resulting in a focused x-ray beam with a larger x-ray flux.

Although FIG. 13 shows two Wolter mirrors of the same size and shape, these need not be the same dimensions, but may have different focal lengths. By selecting appropriate focal length, the x-ray optical train can be designed to demagnify the x-ray source to produce a small focused x-ray beam on to the sample or magnify the x-ray source to produce a large focused beam on to the sample.

Likewise, although only certain embodiments of a linear accumulation x-ray source have been illustrated, other embodiments of the linear accumulation x-ray sources can be used as well.

In many embodiments, the optical train additionally comprises at least one absorbing beam collimator, such as a beam stop, aperture, or slit, used in conjunction with one or more of the optical elements as previously described. These collimators are typically made using materials that are highly absorbing to the bandwidth of x-ray energies of interest. This is to meet the requirements of certain embodiments that the angular convergence of the focused beam in the scattering plane to be less than the critical angle for total reflection for surface sensitivity.

Figure 14A:
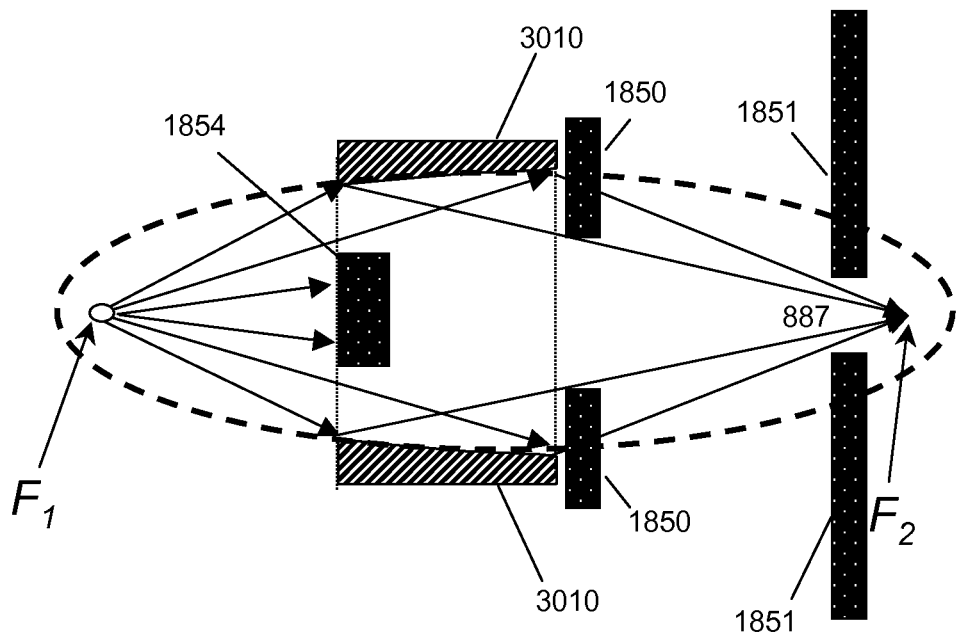
FIG. 14A illustrates a side view cross-sections of a portion of an embodiment of the invention using collimating apertures or slits.

FIG. 14A illustrates a cross-section of an optical train taken along the scattering plane, showing a central beam stop 1854 that blocks non-reflected x-rays passing through the center of the optic 3010. Additionally or alternatively, a collimating slit or aperture 1851 may be used to remove the unreflected x-rays. Furthermore, a slit 1850 may be positioned behind the x-ray mirror 3010 and configured to block portion of the x-rays reflected by the x-ray mirror 3010. The slit opening width is selected to obtain a predetermined angular convergence of the focused x-ray beam in the scattering plane, which should be smaller than the critical angle for total reflection for a given experiment.

Figure 14B:
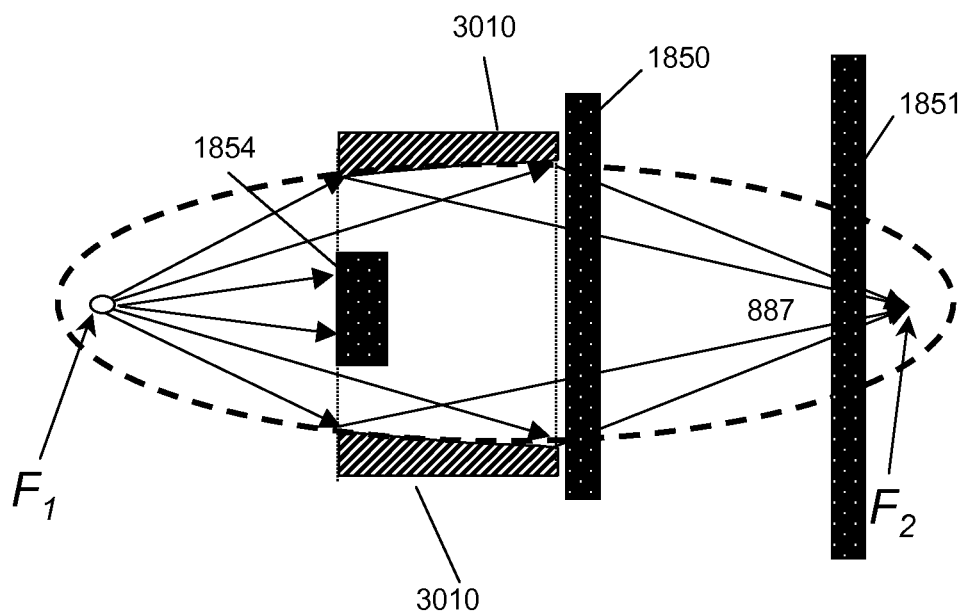
FIG. 14B illustrates top view cross-sections of a portion of an embodiment of the invention using collimating apertures or slits.
Figure 14C:
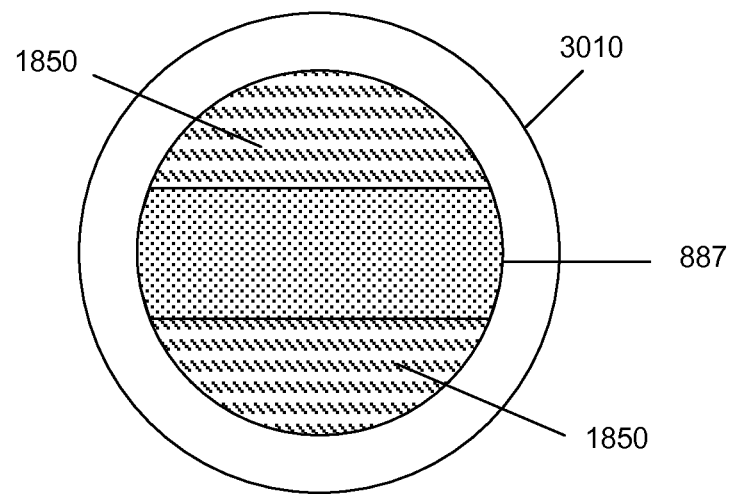
FIG. 14C illustrates a schematic end view of the x-rays for the embodiment illustrated in FIGS. 14A and 14B.

FIG. 14B illustrates a top-down view of the optical train of FIG. 14A in the plane parallel to the sample surface. FIG. 14C illustrates a cross-section of the exit of the axially symmetric optic 3310, indicating the region 887 where reflected x-rays are uncollimated and regions 1850 at the top and bottom in which the x-ray are collimated. The opening width of the slit or aperture 1850 that determines the region 887 is selected to achieve a predetermined angular convergence angle. In FIG. 14B, the center of the aperture or slit is positioned at the center of the x-ray mirror 3010 and its long opening is aligned to perpendicular to the scattering plane. In some embodiments, the aperture or slit 1850 may not be positioned at the center and may either be or act as a knife edge, as the primary goal of the aperture or slit 1850 is to set an upper limit of the angular incidence of the x-rays.

Note that although FIG. 14B illustrates an embodiment using an ellipsoidal mirror, mirrors with any reflecting surface profile may be used in embodiments of the invention.

Figure 15:
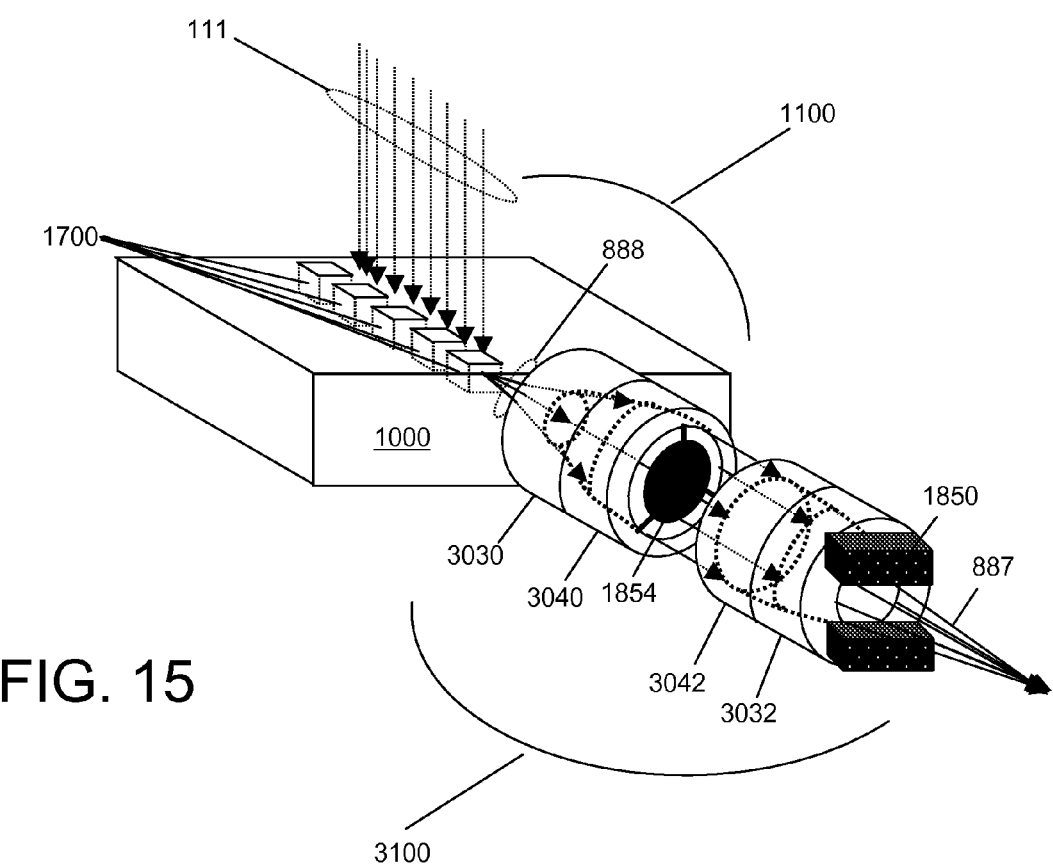
FIG. 15 illustrates a perspective view of a portion of an embodiment of the invention with a linear accumulation source and an optical train.

FIG. 15 illustrates a perspective view of a x-ray source 1100 and optical train sub-sources 1700 providing x-rays that are aligned to produce an x-ray beam with linear accumulation with a focusing optical train 3100 comprising a first optical component of a collimating Wolter type I mirror with mirror surfaces 3030 and 3040. A beam stop 1854 is placed to remove the non-reflected x-rays. A second Wolter type I optical element comprising a first mirror surface 3042 and a second mirror surface 3032 focuses the beam 887. The slit 1850 limits the angle of convergence of the focused beam 887 incident upon the sample.

Figure 16:
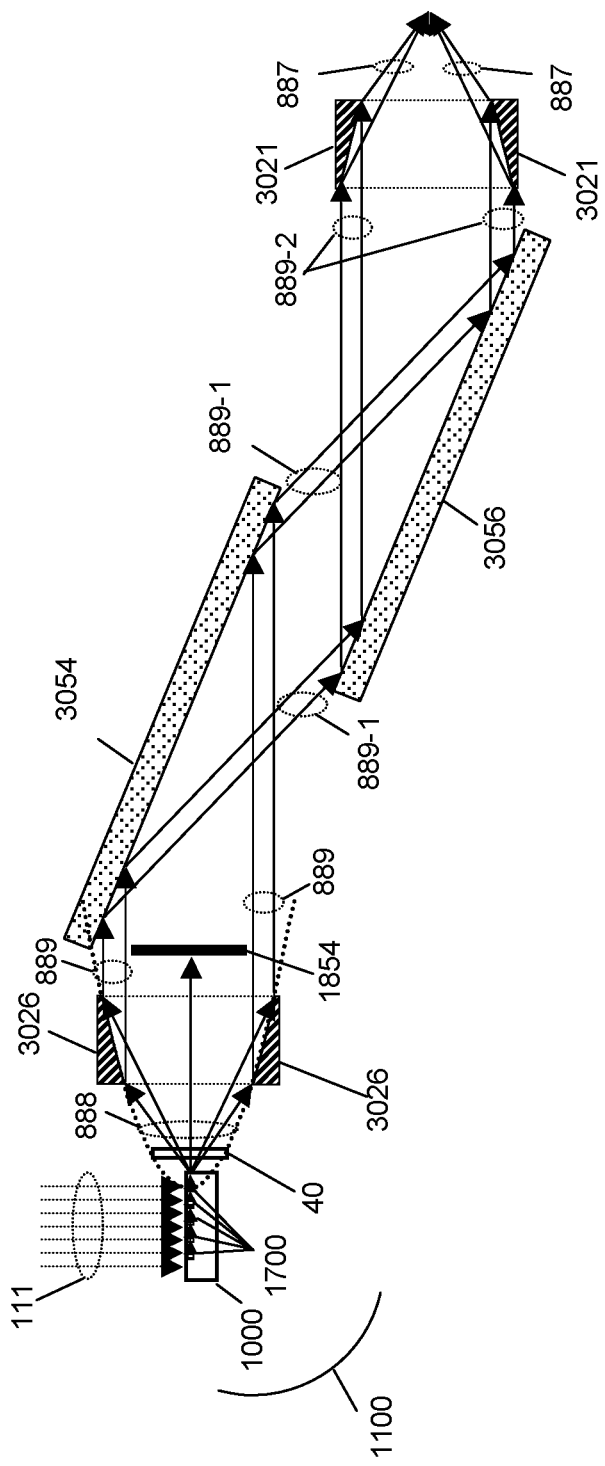
FIG. 16 illustrates a cross-section of a portion of an embodiment of the invention having a double crystal monochromator.

FIG. 16 schematically illustrates a portion of an embodiment of the present invention that may be used to obtain a bright, focused x-ray beam with a narrow energy spectrum, comprising a linear accumulation x-ray source 1100 generating bright x-rays along a predetermined axis, a first paraboloidal x-ray mirror 3026 which is properly positioned and aligned with x-ray source 1100 to collect x-rays from the source 1100 and produce a collimated x-ray beam 889; a central beam stop 1854 that blocks non-reflected x-rays passing through the center of the optic 3026; a double crystal monochromator comprising a first crystal 3054 and second crystal 3056 is configured to monochromatize the incident x-ray beam 889 to obtain a monochromatized x-ray beam 889-2 with predetermined x-ray energy, and a second paraboloidal x-ray mirror 3021 which is configured in reverse orientation with the first paraboloidal x-ray mirror 3026 to receive the monochromatized x-ray beam 889-2 and produce a focused x-ray beam for incidence on the sample.

The crystal monochromator may be of any type known to the art, such as common U-shaped (channel-cut) crystals comprised of silicon (Si) or germanium (Ge) single crystal or parallel semiconductor crystal plates. The double crystal monochromator is rotated to change the incidence angle of the collimated x-ray beam, which enables selection of x-ray energies of interest by changing angle of diffraction. The surface material of one or both mirror components may be glass, or coated either with a high mass density material to increase the critical angle for total reflection to collect more x-rays from the linear accumulation x-ray source. It should be noted that although a second focusing optic is shown, in some embodiments, there is only a single collimating optic and a double crystal monochromator. The monochromatized and collimated beam is then incident upon the sample without passing through an additional optical element.

In various embodiments of the x-ray surface analysis and measurement apparatus, the x-ray optical train may additionally comprise a spectral filter such as a thin foil made from a material containing a large atomic fraction of element with an absorption edge slightly above the predetermined x-ray energy of the x-ray beam, such as a thin nickel (Ni) foil for copper (Cu) Ka characteristic lines.

In various preferred embodiments of the presentation invention, the x-ray optical train has a point spread function that is smaller than or comparable to the effective source size of the linear accumulation x-ray source to preserve the source brightness.

Alternatively, the x-ray optical train may comprise a doubly curved crystal optic (for example, the Doubly-Bent Focusing Crystal Optic produced by XOS Inc. of Albany, N.Y.). Additionally or alternatively, the x-ray optical train may comprise multiple elements to focus and monochromatize the beam, such as the combination of a coated cylindrical mirror and a double multilayer monochromator [see, for example, Pianetta et al. "application of synchrotron radiation to TXRF analysis of metal contamination on silicon wafer surfaces" *Thin Solid Films* vol. 373, pp. 222-226 (2000)].

The x-ray beam after the x-ray optical train impinges upon a sample 240 (as was illustrated in FIG. 1) at a grazing angle less than the critical angle of the substrate at the incident x-ray energy. The sample is optionally placed upon a sample stage capable of moving in three orthogonal directions (X, Y, and Z) for locating a single analysis and/or measurement point or for mapping over a large area. Preferably, the stage accommodates large flat planar shapes, such as wafers and other reflective media (e.g. quartz glass for liquid samples to be prepared as a thin film or for microparticles located upon the flat substrate). Optionally, sample preparation and loading systems known to the art can be added, including robotic or automated sample loading and transfer systems or vapor phase deposition. In some embodiments, additional or alternative electromechanical systems are implemented to move the source, optical train, and detector either independently or simultaneously.

Example applications include analysis of material contamination of semiconductor wafers, elemental composition analysis and thin film thickness measurement during semiconductor device manufacturing processes, such as dielectric materials, copper diffusion barriers, composition analysis and size and size distribution characterization of nanoparticles deposited on a flat surface, trace element detection and analysis in solutions and solid (with digestion and deposition on a flat and smooth surface) in forensics, pharmaceuticals, food, environmental samples, nanoparticles, and biological tissue In various embodiments, the x-ray surface analysis and measurement apparatus is configured to perform XRR, TXRF, GIXRD, GID, and GISAXS, singularly, sequentially, or simultaneously in combination all or a subset of all. The brighter sources and the various embodiments of optical train also described herein, as well as in the other co-pending applications cited by reference herein, may be combined with any number of these established techniques, including those cited herein, to produce a surface analysis and measurement system that is faster, and with a stronger signal and therefore a better signal/noise ratio, due to the additional flux of x-rays available from a source using linear accumulation. Those skilled in the art will recognize that these combinations of techniques will, along with the source using linear accumulation and an optical train that can collect the x-rays so generated efficiently, will therefore constitute a new system for use in performing XRR, TXRF, GIXRD, GID, and/or GISAXS, singularly, sequentially, or simultaneously in combination all or a subset of all.

Various embodiments of the present invention comprises at least one detector to receive x-rays from the sample in response to the interaction of the incident x-ray beam with the sample, and produces signals indicative of properties of the sample. The x-ray signals from the sample may include characteristic fluorescent x-rays resulting from absorption of the incident x-rays, diffracted, scattered, and reflected x-rays.

In various embodiments, when the x-ray surface analysis and measurement apparatus is configured for TXRF, the x-ray detector 2900 as was shown in FIG. 1 may include one or more of various x-ray detectors known in the art, such as solid state energy dispersive detectors (including lithium drift silicon detector (Si(Li)), silicon drift detector (SSD) and variants, silicon PIN diodes, microcalorimeters, and wavelength dispersive spectrometer comprising a wavelength dispersive component based on Bragg reflection in combination with any detector capable of detecting x-rays. For low energy x-ray detection (such as fluorescent lines of low Z elements), a detector with a highly transmissive window or a windowless detector for low energy x-rays is preferred. Qualitative/quantitative analysis is performed based on the intensity of the fluorescent x-rays measured by the spectrometer, sample preparation, and parameters of the incident x-ray beam.

Data acquisition procedures known to the art are used including aligning the sample relative to the incident x-ray beam in position and angle. Data analysis methods known to the art including absolute and relative quantification are used. For example, qualitative/quantitative analysis is performed based on the intensity of the fluorescent x-rays measured by the spectrometer, sample preparation, and parameters of the incident x-ray beam. Many analysis examples and sample preparation techniques have been well established and published, including the qualitative/quantitative analysis of a specimen placed on a wafer surface.

In some preferred embodiments, the fluorescence signal obtained is then analyzed by established techniques or software packages similar to common XRF and TXRF analysis packages, such as WinAxil (Canberra University, Australia) or Rigaku TXRF Software (Rigaku Corp., Tokyo, Japan).

In various embodiments, when the surface analysis and measurement apparatus is configured for XRR, GIXRD, GID, and/or GISAXS, the x-ray detector 2900-R of FIG. 1 may include one or more position sensitive array detectors known in the art, including line and 2D array detectors. Such examples of position-sensitive detectors include photodiode detectors, scintillator-type and gas-filled array detectors. In some embodiments, the detector includes one or more detector elements of any type that detects x-rays, including proportional and avalanche detectors or energy-dispersive elements.

In various embodiments enabling TXRF analysis, use of an x-ray imaging optic between the detector and the sample to define a small analysis volume. A preferred embodiment is to use an x-ray imaging optic with a small aperture or slit to obtain even smaller analysis volume. Furthermore, by selecting an appropriate E, making use of the wider choice of x-ray energies afforded by the new x-ray source, the cross-section of element(s) of interest is optimized. Additionally or alternatively, the incident x-ray energy can be purposely selected to reduce x-ray fluorescence signal from other element(s) in the sample and/or the substrate. Alternatively, a thin film spectra filter to obtain a desired x-ray spectra know in the art can also be used.

In some embodiments that enable XRR analysis, it is preferred that a double crystal monochromator is added and collimating elements are removed from the optical train such that the incident beam is focused at a large angles of incidence, including ones that are greater than the critical angle. This allows the processor to interpret the signals from a position-sensitive detector corresponding to the intensity and angle of reflection of the monochromatic x-rays sensed to determine, based on well-established methods, various properties of the surface layer(s), including thickness, density, and smoothness.

In some embodiments that enable GIXRD analysis, it is preferred that the radiation source and detector array are positioned so that the array senses x-rays that are diffracted from the surface in a vicinity of the Bragg angle of the sample. A motion assembly system may be employed to move the source, sample, and detector, singularly or in combination. It is preferred in some embodiments to have a focusing optical train with a monochromator to enable high resolution XRD with the incident x-ray beam exceeding the critical angle of the sample. In other embodiments, it is preferred that the optical train is collimating and placed at a high angle. In the most preferred embodiments, it is preferred to have a collimating optical train for GIXRD placed at a low grazing incidence angle.

In some embodiments that enable GISAXS measurements, the detector is preferably placed within the sample plane of the surface to enable measurement of scattering as a function of azimuth and the source and optical train are positioned such that the sample is illuminated with a collimated beam of incident x-rays at low angles.

Limitations and Extensions

With this application, several embodiments of the invention, including the best mode contemplated by the inventors, have been disclosed. It will be recognized that, while specific embodiments may be presented, elements discussed in detail only for some embodiments may also be applied to others. Elements in the co-pending applications incorporated by reference into this application, such as, for example, polycapillary optics, may also be incorporated into embodiments of the invention disclosed herein.

While specific materials, designs, configurations have been set forth to describe this invention and the preferred embodiments, such descriptions are not intended to be limiting. Modifications and changes may be apparent to those skilled in the art, and it is intended that this invention be limited only by the scope of the appended claims.

We claim:
1. An x-ray system for analyzing a sample, comprising:
   at least one x-ray source comprising:
   a vacuum chamber;
   a window transparent to x-rays attached to the wall of the vacuum chamber;
   and, within the vacuum chamber:
   at least one electron beam emitter, and
   an anode target comprising:
   a substrate comprising a first selected material, and
      a planar first surface, from which thickness is measured in a direction perpendicular to the first planar surface, and two orthogonal lateral dimensions are measured parallel to the first planar surface; and a plurality of discrete structures embedded into the first planar surface of the substrate such that each of the plurality of discrete structures is in thermal contact with the substrate,
the plurality of discrete structures comprising:
one or more materials selected for its x-ray generation properties;
in which at least two of the plurality of discrete structures are arranged on a predetermined axis;
in which the predetermined axis is parallel to the first planar surface of the substrate;
in which the predetermined axis passes through the first window;
in which each of the discrete structures has a thickness of less than 20 microns, and
in which each of the plurality of discrete structures has a lateral dimension in the direction of the predetermined axis of less than 50 microns; and
a means of directing electrons emitted by the at least one electron beam emitter onto the at least two arranged discrete structures such that x-rays are generated from each of the at least two arranged discrete structures;
in which at least a portion of the generated x-rays propagating on the predetermined axis from each of the two arranged discrete structures is transmitted through the window;
and additionally comprising:
an x-ray optical system
having an optical axis aligned relative to said predetermined axis, said optical system positioned to collect diverging accumulated x-rays from said at least two arranged discrete structures in the x-ray source
and to condition and create an x-ray beam with predetermined properties;
said optical system additionally comprising a central beam stop positioned to block x-rays propagating parallel to the optical axis;
a means to direct the x-ray beam to be incident onto an area of the surface of a sample at a grazing angle less than the critical angle with the surface;
at least one detector positioned to detect the intensity of the x-rays emerging from the sample and generate electrical signals; and
a signal processor to analyze the electrical signals to obtain information about at least one of:
composition, concentration, quantity, and film thickness.

2. The x-ray system of claim 1,
in which said at least one detector is positioned to detect fluorescent x-rays that are radiated by the sample;
and additionally comprising:
at least one additional detector to detect x-rays reflected from the surface of the sample.

3. The x-ray system of claim 1, in which said x-ray beam with predetermined properties has the property of being focused to a single spot with a spot size smaller than 300 microns; and in which the focused x-ray spot corresponds to a predetermined position on the surface of the sample.

4. The x-ray system of claim 1, in which said predetermined axis and said optical axis are coincident.

5. The x-ray system of claim 1, in which said optical system comprises a total external reflection based x-ray optic.

6. The x-ray system of claim 1, in which said substrate comprising a first selected material has a thermal conductivity greater than 0.1 W m$^{-1\circ}$ C.$^{-1}$.

7. The x-ray system of claim 1, in which the first selected material is selected from the group consisting of:
beryllium, diamond, graphite, silicon, boron nitride, silicon carbide, sapphire, and diamond-like carbon.

8. The x-ray system of claim 1, in which the one or more materials selected for its x-ray generation properties are selected from the group consisting of:
aluminum, titanium, vanadium, chromium, manganese, iron, cobalt, nickel, copper, gallium, zinc, yttrium, zirconium, molybdenum, niobium, ruthenium, rhodium, palladium, silver, tin, iridium, tantalum, tungsten, indium, cesium, barium, gold, platinum, lead, and combinations and alloys thereof.

9. An x-ray measurement system, comprising:
an x-ray source, comprising:
a vacuum chamber;
a window transparent to x-rays attached to the wall of the vacuum chamber;
and, within the vacuum chamber:
at least one electron beam emitter, and
an anode target comprising:
a substrate comprising a first selected material, and
a planar first surface,
from which thickness is measured in a direction perpendicular to the first planar surface, and
two orthogonal lateral dimensions are measured parallel to the first planar surface; and
a plurality of discrete structures embedded into the first planar surface of the substrate such that each of the plurality of discrete structures is in thermal contact with the substrate,
the plurality of discrete structures comprising:
one or more materials selected for its x-ray generation properties;
in which at least two of the plurality of discrete structures are arranged on a predetermined axis;
in which the predetermined axis is parallel to the first planar surface of the substrate;
in which the predetermined axis passes through the first window;
in which each of the discrete structures has a thickness of less than 20 microns, and
in which each of the plurality of discrete structures has a lateral dimension in the direction of the predetermined axis of less than 50 microns; and
a means of directing electrons emitted by the at least one electron beam emitter onto the at least two arranged discrete structures such that x-rays are generated from each of the at least two arranged discrete structures;
in which at least a portion of the generated x-rays propagating on the predetermined axis from each of the at least two arranged discrete structures is transmitted through the window;
and additionally comprising:
an optical train having an optical axis to collect diverging x-rays generated by said at least two of the plurality of discrete structures in the anode target, and that produces an x-ray beam with predetermined beam properties;
said optical train additionally comprising a central beam stop positioned to block x-rays propagating parallel to said optical axis;
a mount to hold an object to be investigated, positioned such that the x-ray beam will be incident onto an area of the surface of the object at a grazing angle less than the critical angle with the surface;

a detector to measure x-rays emerging from the object when x-rays are incident on the object.

10. The system of claim 9, in which said detector is positioned to detect fluorescent x-rays that are radiated by the sample;
and additionally comprising:
an additional detector to measure the intensity of the x-rays reflected from the object.

11. The system of claim 9, in which each lateral dimension parallel to said first planar surface for each of said at least two arranged discrete structures is less than 50 microns.

12. The system of claim 9, in which the plurality of discrete structures are arranged in a linear array along said predetermined axis; and
the optical axis of the optical train is also aligned along said predetermined axis.

13. The system of claim 9, in which the first selected material is selected from the group consisting of:
beryllium, diamond, graphite, silicon, boron nitride, silicon carbide, sapphire, and diamond-like carbon.

14. The system of claim 9, in which the one or more materials selected for its x-ray generation properties is selected from the group consisting of:
aluminum, titanium, vanadium, chromium, manganese, iron, cobalt, nickel, copper, gallium, zinc, yttrium, zirconium, molybdenum, niobium, ruthenium, rhodium, palladium, silver, tin, iridium, tantalum, tungsten, indium, cesium, barium, gold, platinum, lead and combinations and alloys thereof.

15. The system of claim 9, additionally comprising:
an additional plurality of discrete structures aligned along said predetermined axis comprising a third material selected for its x-ray generation properties,
in which each of the additional plurality of discrete structures is in thermal contact with the substrate, and
in which at least two of the additional plurality of discrete structures has a lateral dimension in the direction of the predetermined axis of less than 50 microns.

16. The system of claim 15, in which the third material is selected from the group consisting of:
aluminum, titanium, vanadium, chromium, manganese, iron, cobalt, nickel, copper, gallium, zinc, yttrium, zirconium, molybdenum, niobium, ruthenium, rhodium, palladium, silver, tin, iridium, tantalum, tungsten, indium, cesium, barium, gold, platinum, lead and combinations and alloys thereof.

17. The system of claim 9, in which the plurality of discrete structures are arranged such that x-rays generated by a predetermined number of the plurality of discrete structures when exposed to an electron beam from the electron beam emitter are transmitted through a predetermined one of the discrete structure selected from the plurality of discrete structures.

18. The system of claim 9, comprising
an additional number of electron emitters and,
an additional number of anode targets,
with each anode target corresponding to a single electron emitter, such that each electron emitter is aligned to provide an electron beam to bombard the corresponding anode target to generate x-rays; and
the additional number of anode targets are aligned with each other and with said one anode target, such that the positions at which x-rays are generated in said one anode target and said additional number of anode targets are aligned along said predetermined axis; and
the optical train is also aligned along said predetermined axis.

19. The system of claim 9, in which the optical train comprises at least one axially symmetric x-ray reflector with a surface corresponding to a quadric surface.

20. The system of claim 19, in which the quadric surface is selected from the group consisting of:
a spheroid, an ellipsoid, a paraboloid, a hyperboloid, an elliptic cylinder, a circular cylinder, an elliptic cone, and a circular cone.

21. The system of claim 9, in which the optical train comprises a type I Wolter x-ray optic.

22. The system of claim 9, in which the predetermined x-ray beam properties are those of a collimated x-ray beam.

23. The system of claim 9, in which the predetermined x-ray beam properties are those of a focused x-ray beam.

24. The system of claim 9, in which the detector is a silicon drift detector.

25. The x-ray measurement system of claim 9, in which said substrate comprising a first selected material has a thermal conductivity greater than $0.1$ W $m^{-1\circ}$ C.$^{-1}$.

26. An x-ray measurement system, comprising:
an x-ray source comprising:
a vacuum chamber;
a first window transparent to x-rays attached to the wall of the vacuum chamber; and,
within the vacuum chamber, one or more electron emitters; and
a plurality of x-ray targets;
with each target comprising a material selected for its x-ray generating properties, and in which at least one dimension of said material is less than 20 microns; and
in which said one or more electron emitters and said plurality of x-ray targets are aligned such that bombardment of electrons on said x-ray targets produces x-ray sub-sources such that said sub-sources are aligned along an axis that passes through the first window; and
at least one x-ray imaging optical element, said x-ray imaging optical element positioned such that x-rays generated by one of said x-ray sub-sources are collected by said x-ray imaging optical element and focused onto a position corresponding to one of the other x-ray sub-sources;
said system additionally comprising:
an optical train comprising:
at least one optical element with an optical axis aligned with said axis such that the at least one optical element collects diverging x-rays generated by said sub-sources and that produces an x-ray beam with predetermined beam properties;
a central beam stop positioned to block x-rays propagating parallel to said optical axis;
a mount to hold an object to be investigated positioned such that the x-ray beam will be incident onto an area of the surface of the object at a grazing angle less than the critical angle with the surface; and
a detector to measure x-rays emerging from the object when x-rays are incident on the object.

27. The x-ray measurement system of claim 26, in which each x-ray target comprises a plurality of discrete structures embedded in the substrate, and said substrate comprises a material with a thermal conductivity greater than $0.1$ W $m^{-1\circ}$ C.$^{-1}$;
and in which said plurality of discrete structures comprises a material selected for its x-ray generating properties.

28. The x-ray measurement system of claim 26, in which the x-rays generated by at least one of said x-ray sub-sources are collected by said at least one x-ray imaging optical element and focused onto a position corresponding to an adjacent said x-ray sub-source.

29. The x-ray measurement system of claim 28, in which the at least one x-ray imaging optical element comprises a total external reflection based x-ray reflectors.

30. The x-ray measurement system of claim 29, in which the at least one x-ray imaging optical element comprises an ellipsoidal capillary optic having an ellipsoidal surface, said optic positioned such that the positions of the foci of the ellipsoidal surface respectively correspond to the positions of two adjacent said sub-sources.

31. The x-ray measurement system of claim 29, in which the at least one x-ray imaging optical element comprises at least one paraboloidal capillary optic having a paraboloidal surface, said optic positioned such that the position of the focus of the paraboloidal surface corresponds to the position of one of said sub-sources.

* * * * *